US010758748B2

(12) United States Patent
Chappelow et al.

(10) Patent No.: US 10,758,748 B2
(45) Date of Patent: *Sep. 1, 2020

(54) VERIFICATION OF LEAF POSITIONS FOR MULTI-LEAF COLLIMATOR USING MULTIPLE VERIFICATION SYSTEMS

(71) Applicant: Accuray Incorporated, Sunnyvale, CA (US)

(72) Inventors: Jonathan Cecil Chappelow, Campbell, CA (US); Petr Jordan, Redwood City, CA (US); Calvin Maurer, San Jose, CA (US); Sarbjit Singh, San Jose, CA (US); Andrew W. Fitting, Fremont, CA (US); Andriy Myronenko, San Mateo, CA (US); Jian Gao, San Jose, CA (US)

(73) Assignee: Accuray Incorporated, Sunnyvale, CA (US)

( * ) Notice: Subject to any disclaimer, the term of this patent is extended or adjusted under 35 U.S.C. 154(b) by 120 days.

This patent is subject to a terminal disclaimer.

(21) Appl. No.: 15/916,068

(22) Filed: Mar. 8, 2018

(65) Prior Publication Data

US 2018/0193671 A1    Jul. 12, 2018

Related U.S. Application Data

(63) Continuation of application No. 15/008,239, filed on Jan. 27, 2016, now Pat. No. 9,943,705.

(Continued)

(51) Int. Cl.
*A61N 5/10* (2006.01)
*G21K 1/04* (2006.01)
*G06T 7/00* (2017.01)

(52) U.S. Cl.
CPC ......... *A61N 5/1049* (2013.01); *A61N 5/1045* (2013.01); *A61N 5/1048* (2013.01);
(Continued)

(58) Field of Classification Search
CPC .. A61N 5/1045; A61N 5/1049; A61N 5/1048; A61N 2005/1054;
(Continued)

(56) References Cited

U.S. PATENT DOCUMENTS

| 4,868,843 A | 9/1989 | Nunan |
| 2005/0179688 A1 | 8/2005 | Chernichenko et al. |

(Continued)

FOREIGN PATENT DOCUMENTS

| JP | 2004-229683 A | 8/2004 |
| JP | 5247565 B2 | 7/2013 |

OTHER PUBLICATIONS

Samant et al. "Automated Verification of Multileaf Collimation (MLC) using a Siemens EPID." Proceedings of the 22nd Annual International Conference of the IEEE Engineering in Medicine and Biology Society, Jul. 23, 2000, pp. 2433-2445 (Year: 2000).*

(Continued)

*Primary Examiner* — Jon Chang
(74) *Attorney, Agent, or Firm* — Womble Bond Dickinson (US) LLP

(57) ABSTRACT

A method includes determining a first estimate of leaf positions for a plurality of leaves of a multi-leaf collimator (MLC) in a reference coordinate space based on an image generated by an image-based aperture verification system, wherein the leaf positions for the plurality of leaves define an aperture for the MLC. The method further includes determining a second estimate of the leaf positions for the plurality of leaves in the reference coordinate space based on data from an additional source. The method further includes verifying the leaf positions for the plurality of leaves based on comparing the first estimate to the second estimate, wherein the leaf positions are verified if the first estimate deviates from the second estimate by less than a threshold value.

16 Claims, 29 Drawing Sheets

Related U.S. Application Data

(60) Provisional application No. 62/175,131, filed on Jun. 12, 2015.

(52) U.S. Cl.
CPC ............ *G06T 7/0012* (2013.01); *G21K 1/046* (2013.01); *A61N 2005/1054* (2013.01); *A61N 2005/1074* (2013.01)

(58) Field of Classification Search
CPC .......... A61N 2005/1074; A61N 5/1067; G06T 7/0012; G06T 2207/30164; G21K 1/046
See application file for complete search history.

(56) References Cited

U.S. PATENT DOCUMENTS

| | | |
|---|---|---|
| 2006/0072849 A1 | 4/2006 | Marc |
| 2008/0298553 A1 | 12/2008 | Takahashi |
| 2009/0010395 A1* | 1/2009 | Ein-Gal .............. A61N 5/1042 378/150 |
| 2012/0215049 A1 | 8/2012 | Otani |
| 2013/0258105 A1 | 10/2013 | Jozsef |
| 2015/0094514 A1 | 4/2015 | Gaudio |

OTHER PUBLICATIONS

USPTO; Non-Final Office Action for U.S. Appl. No. 15/008,232, dated Jun. 30, 2017.
International Search Report and Written Opinion dated Jun. 21, 2016, for PCT/US2016/023456, 14 pages.

\* cited by examiner

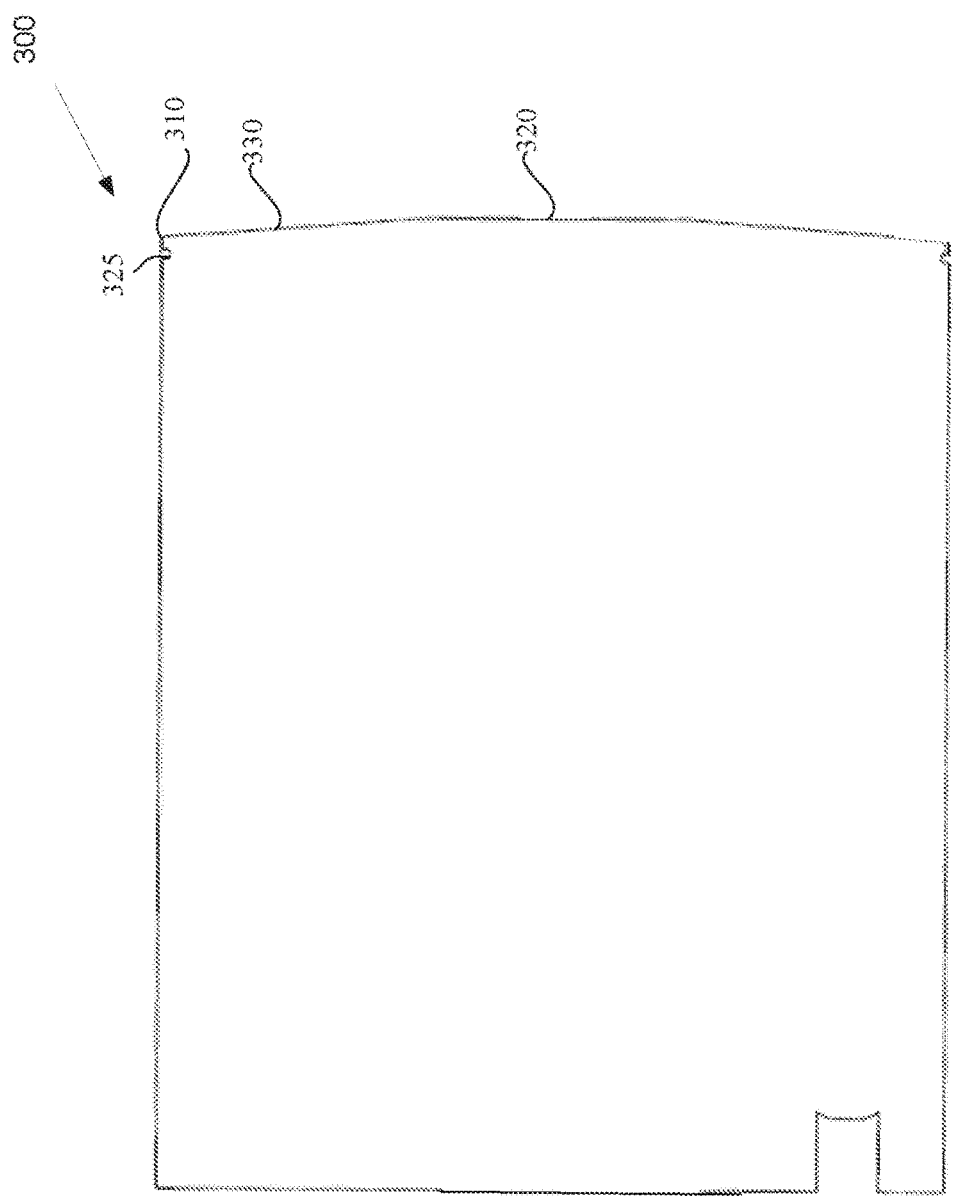

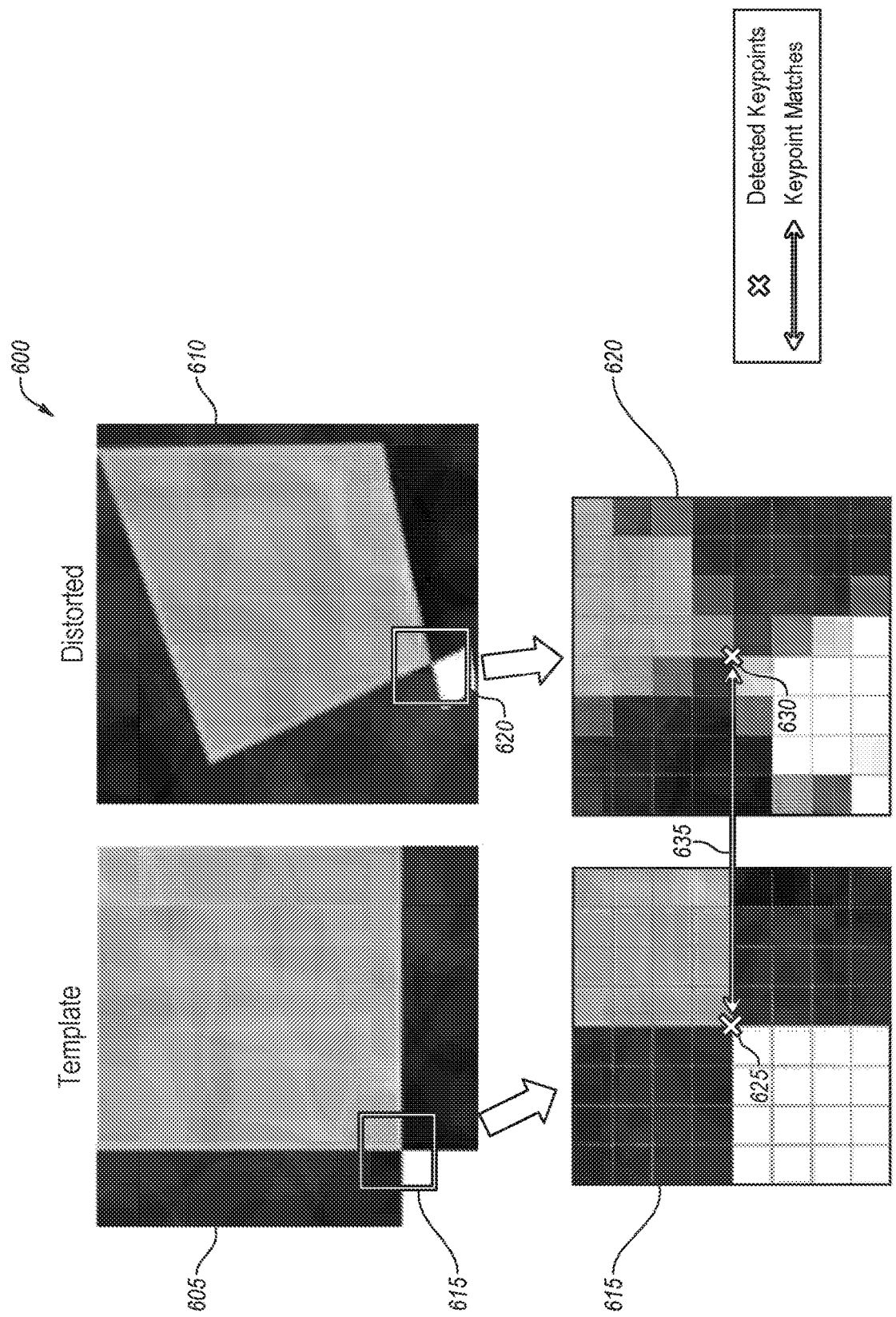

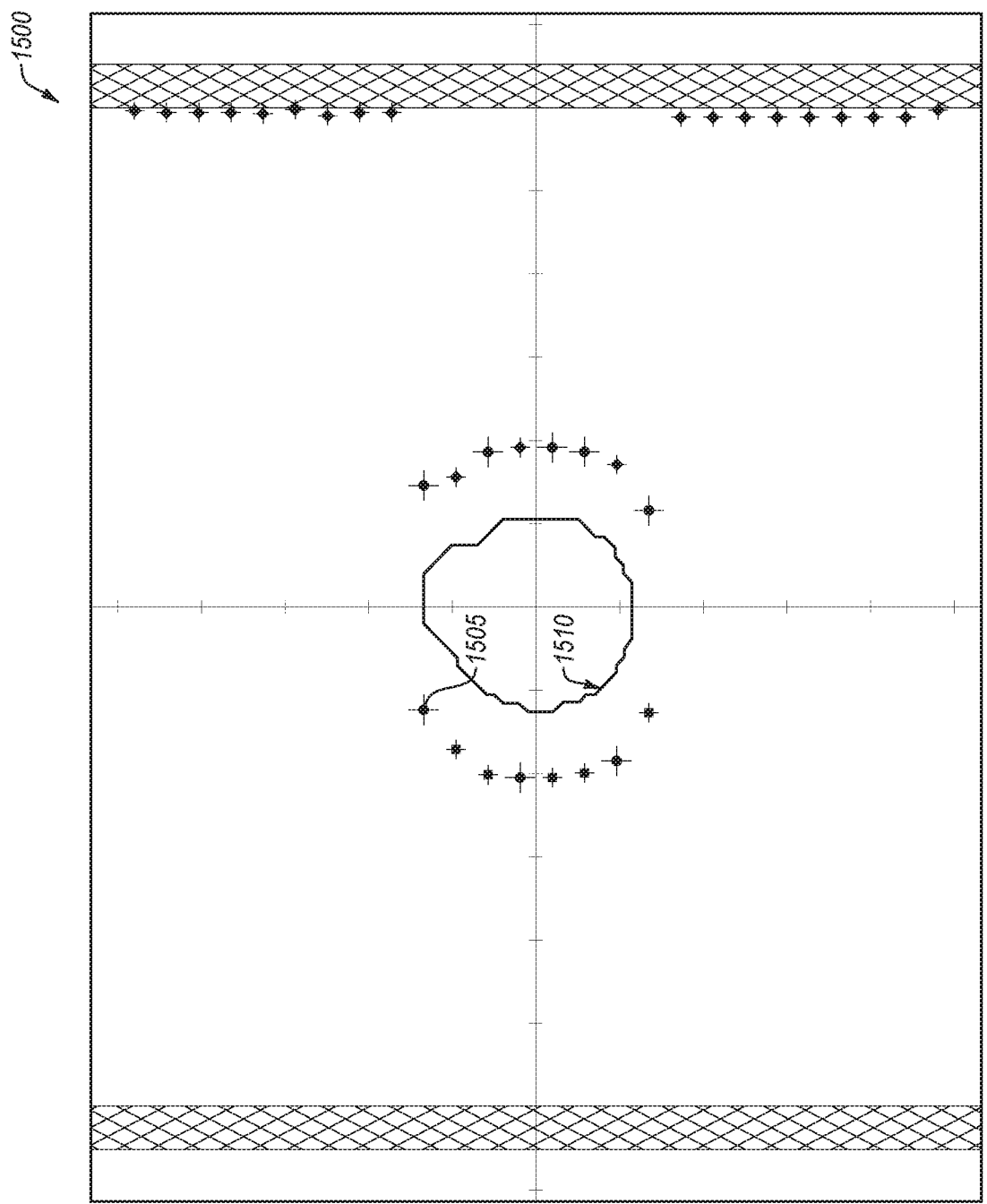

VERIFICATION OF LEAF POSITIONS FOR MULTI-LEAF COLLIMATOR USING MULTIPLE VERIFICATION SYSTEMS

RELATED APPLICATIONS

This patent application is a continuation of U.S. application Ser. No. 15/008,239, filed Jan. 27, 2016, now issued as U.S. Pat. No. 9,943,705 on Apr. 17, 2018, which claims the benefit under 35 U.S.C. § 119(e) of U.S. Provisional Application No. 62/175,131, filed Jun. 12, 2015, the entire contents of which are hereby incorporated by reference.

TECHNICAL FIELD

Embodiments of the present invention relate to multi-leaf collimators (MLCs) and, in particular, to an MLC with an image-based aperture verification system.

BACKGROUND

Collimators are frequently used in radiation treatment for shaping a beam of highly energized particles, referred to as a treatment beam. Some radiation treatment systems use a variable aperture collimator called a multi-leaf collimator (MLC). A multi-leaf collimator is a collimator that is made up of a collection of individual leaves that can move independently in and out of the path of the treatment beam. For conformal radiotherapy and radiosurgery, the MLC enables conformal shaping of the treatment beam (e.g., to match borders of a target). In the MLC, each leaf is typically actuated by its own motor, and has its own displacement gauge to precisely control the position of the leaf. To ensure accuracy, each individual displacement gauge of each leaf must be calibrated. Additionally, MLCs are highly complex, and susceptible to numerous avenues of failure.

BRIEF DESCRIPTION OF THE DRAWINGS

Embodiments of the present invention are illustrated by way of example, and not by way of limitation, in the figures of the accompanying drawings.

FIG. 3 illustrates a side view of a leaf for a multi-leaf collimator, in accordance with one embodiment.

FIG. 6 illustrates an example keypoint match between a corner on a template image and the same corner on an oblique-view image, in accordance with one embodiment.

FIG. 15A illustrates a diagram showing detection markers for leaves of an MLC and a tumor contour, in accordance with embodiments.

DETAILED DESCRIPTION

Described herein is a multi-leaf collimator (MLC) with an internal image-based aperture verification system. The MLC includes a housing that houses multiple leaves that are movable to adjust an aperture of the MLC. The housing additionally houses an image sensor that generates images of the leaves. These images can be used to verify positions of the leaves, and thus to verify the aperture of the MLC.

Also described are methods of applying such an image-based aperture verification system for an MLC. In one embodiment, an image sensor disposed within the MLC generates a distorted oblique-view image of an aperture for the MLC. A processing device then transforms the distorted oblique-view image into a non-distorted top-view image in a reference coordinate space (RCS). This may be performed by transforming the oblique-view image via a transformation matrix or other geometric transformation parameters, which may have been generated during calibration of the MLC. The processing device may then determine whether the estimated aperture based on the non-distorted top-view image is consistent with the aperture of the MLC specified in the treatment plan.

In another embodiment, a processing device determines a first estimate of leaf positions for leaves of an MLC based on a first or primary aperture verification system, wherein the leaf positions for the leaves define an aperture for the MLC. The processing device further determines a second estimate of leaf positions for leaves of the MLC based on an image generated by an image-based aperture verification system. The processing device then maps the first estimate and the second estimate to a common reference coordinate space and verifies the leaf positions for the leaves based on comparing the first estimate to the second estimate, wherein the leaf positions are verified if the first estimate deviates from the second estimate by less than a threshold value. The processing device may additionally generate a pictorial representation of the first estimate, display the image generated by the image-based aperture verification system, and display an overlay of the pictorial representation over the image. In addition, the processing device may generate an additional pictorial representation of the second estimate and display an overlay of the additional pictorial representation over the image.

Use of the image-based aperture verification system provides the advantage of a user being able to visually inspect an aperture of the MLC and compare the aperture to an aperture specified in a treatment plan and/or to an aperture determined from another aperture verification system. Such visual inspection enables users to make their own determination as to whether a current aperture is correct without relying solely on a status output by the MLC. Thus, a user may have a higher sense of security that the aperture is correct before committing to deliver radiation to a patient.

Figure 1:
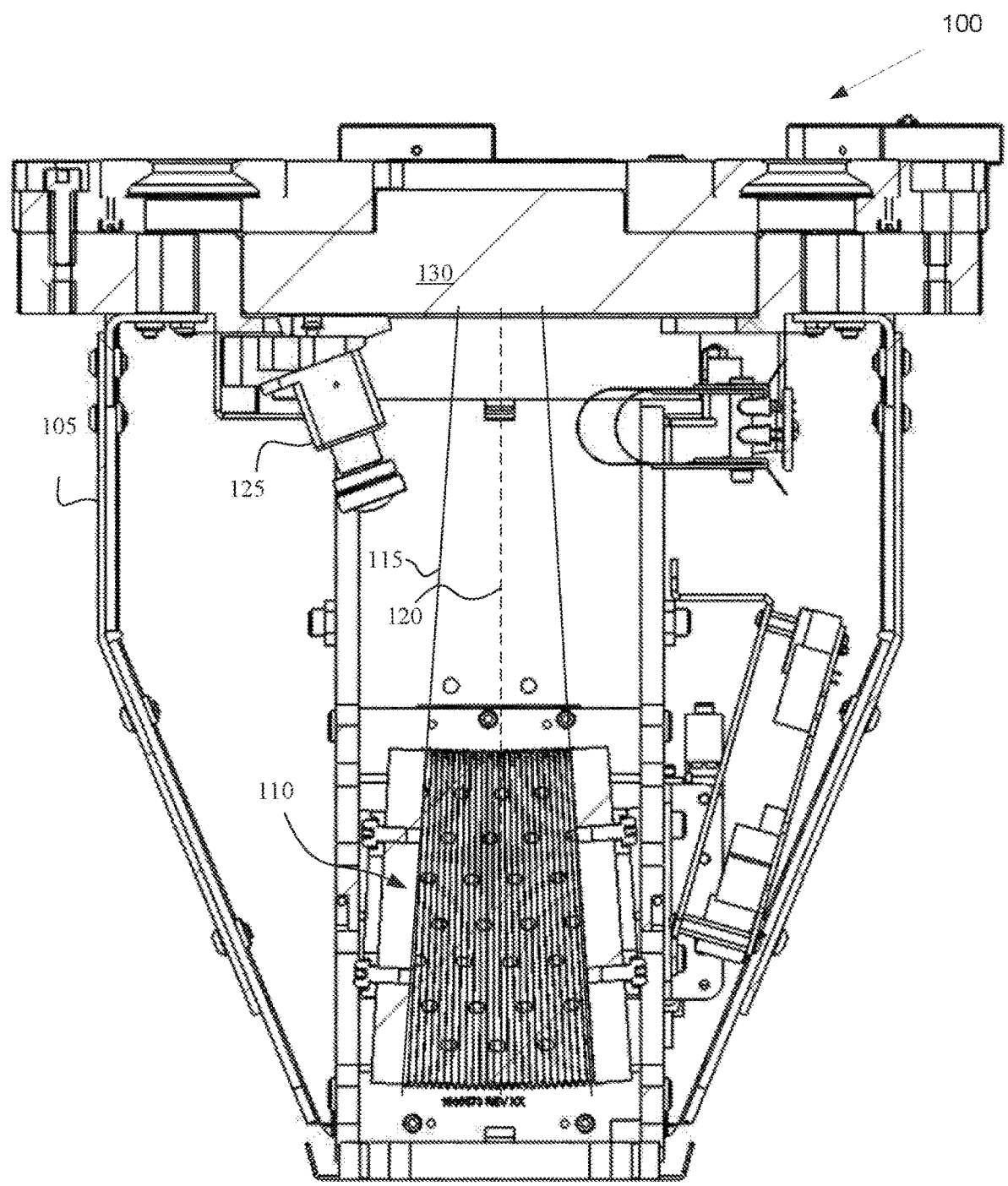
FIG. 1 illustrates a cross-sectional side view of an example multi-leaf collimator, in accordance with one embodiment of the present invention.

FIG. 1 illustrates an example multi-leaf collimator (MLC) 100, in accordance with one embodiment of the present invention. MLC 100 is a collimator that is made up of a patient plane shield 130 and a collection of individual collimation leaves 110 that are disposed within a housing 105. The patient plane shield 130 provides an intermediate radiation shield and additional collimation of a radiation beam within the MLC before the radiation beam reaches the collimation leaves 110. One example MLC includes up to 41 leaf pairs each having a thickness of up to about 1.2 mm. Another example MLC includes up to 26 leaf pairs each having a thickness of greater than 1.9 mm. Many other configurations of MLCs may be used, with any number of leaves having various thicknesses. In one embodiment, the collimation leaves 110 are made of tungsten.

The collimation leaves 110 may all lie on a plane that is normal to a radiation beam axis 120. Alternatively, the collimation leaves may lie on a plane that has a slight tilt with reference to the radiation beam axis. Such collimation leaves may lie on a plane that has a deviation from 90 degrees to the radiation beam axis of up to about 0.5 degrees. This may improve inter-leaf radiation leakage performance in some instances. A plane defined by surfaces of the collimation leaves 110 may be a known fixed distance from the image sensor 125 and from a radiation source (e.g., about 400 mm from a radiation source in one embodiment). Note that in some embodiments the leaves have a divergent shape in which the proximal leaf thickness is lower than the distal leaf thickness. This may cause a surface of the leaves to be a curved surface rather than a plane. For example, the inside of the MLC may have a slightly concave surface, while the outside may be slightly convex. The shape of the plane could be characterized and thus corrected for on the image, if needed. For simplicity of explanation the surface of the leaves will be referred to as a plane herein, with the understanding that in some instances it may be a curved surface. In one embodiment, each of the collimation leaves 110 can move independently in and out of the path 115 of a treatment beam. As shown, the treatment beam is a diverging beam. In a further embodiment, each collimation leaf can be moved along a path that follows a linear trajectory on the plane. The linear trajectories of all of the collimation leaves may be parallel (or approximately parallel) to one another.

For conformal radiation treatment, the MLC 100 enables conformal shaping of the treatment beam based on borders of a target by moving the leaves 110 along their respective linear trajectories to desired positions. The collimation leaves 110 may be arranged in one or more banks of collimation leaves. In one embodiment, the collimation leaves 110 are arranged in a left bank of leaves and a right bank of leaves. Each leaf in the left bank may have an opposing leaf in the right bank. When the collimation leaves 110 are retracted behind the patient plane shield 130 on both sides, then both banks are fully open. When the leaves of one bank extend beyond the patient plane shield 130 (and beyond the path 115 of the radiation beam), those leaves are in the fully closed position.

In the MLC 100, each leaf may be actuated by its own motor. In one embodiment, each leaf has its own displacement gauge or encoder to precisely control the position of the leaf. The displacement gauge or encoder may act as a leaf position verification system for the associated leaf. In one embodiment, the displacement gauge is a linear variable differential transformer (LVDT). One example of an LVDT that may be used is a differential variable reluctance transducer (DVRT) manufactured by MicroStrain®. In another embodiment, the displacement gauge is a rotary variable differential transformer (RVDT). In another embodiment, the encoder is a shaft-mounted incremental rotary encoder (e.g., Encoder MEnc 10, manufactured by Maxon®). The displacement gauge outputs a reading that is dependent on how far a leaf has moved along a guided path. In one embodiment, the displacement gauge outputs a voltage whose value is dependent on the leaf's position. There may be an approximately linear relationship between voltage and displacement. In another embodiment, the displacement gauge outputs a discrete digital count number corresponding to the number of motor rotations from a reference position. In the aggregate, the displacement gauges may act as a first or primary aperture verification system for the MLC 100.

Also disposed within the housing 105 is an image sensor 125. As shown, the image sensor 125 has a position in the MLC 100 that is offset from a beam axis 120 to avoid being in the path 115 of the radiation beam. The image sensor 125 is directed toward the leaves 110 at an oblique angle to the leaves 110. Accordingly, the image sensor 125 generates distorted oblique-view images of the aperture.

The image sensor 125 is one component of an image-based aperture verification system that can be used to show the actual positions of the leaves before, during and after radiation treatment beams are delivered. The image-based aperture verification system may use the images generated by the image sensor 125 along with image processing algorithms performed by a processing device to detect leaf positions. The image sensor 125 may generate a video of the leaves 110 and/or one or more static images of the leaves 110. The image-based aperture verification system may process these images using image processing techniques to determine leaf positions, and may compare these leaf positions to specified leaf positions from a treatment plan, leaf positions measured by another aperture verification system (e.g., leaf positions determined by multiple displacement gauges), and so on. In one embodiment, leaf positions determined by the image-based aperture verification system are compared to leaf positions determined by an MLC motor control system (e.g., that includes a collection of displacement gauges/encoders). Leaf graphics as determined from the MLC motor control system, the treatment plan, and/or the image-based aperture verification system may be superimposed on images generated by the image-based aperture verification system to provide real-time information about leaf positions as the collimation leaves are moving or at rest.

In one embodiment, the image sensor 125 is part of an imaging device that includes the image sensor 125 and additional components (e.g., a remote sensor controller board), and is located apart from additional components of the imaging device so that these additional components will be separated from the radiation beam. Over time, radiation from a radiation beam may damage components of the imaging device. Such damage can be mitigated by dividing the imaging device into image sensor 125 and a remote sensor controller board (and potentially other components), and positioning the sensor controller board (and/or other components) away from the radiation beam. In one embodiment, the sensor controller board is located away from the radiation beam, but is still disposed within a housing of an MLC. In another embodiment, the image sensor 125 is disposed within the housing of the MLC, but the sensor controller board is located outside of the housing. In one embodiment, the sensor controller board is located behind a shield that separates the sensor controller board from the radiation beam. In one embodiment, the image sensor 125 is a complementary metal oxide (CMOS) device. In another embodiment, the image sensor 125 is a charge coupled device (CCD).

The position and angle of the image sensor 125 relative to the collimation leaves may cause images generated by the image sensor 125 to be oblique-view images. For example, these images may exhibit a keystone effect. The image-based aperture verification system may include a processing device (not shown) that processes these images to remove lens distortion (e.g., radial lens distortion) and to transform the images from oblique-view images into top-view images that appear to have been taken from a different perspective. The top-view images emulate a view that would be generated if the image sensor were oriented parallel to the beam axis 120 and positioned approximately on the beam axis 120. The oblique-view images that are generated by the image sensor 125 may additionally be optically distorted images (as caused by camera optics). The processing device of the image-based aperture verification system may additionally process the distorted oblique-view images to remove the distortion. This may be performed prior to transforming the perspective of the images from oblique-view to top-view. A non-distorted (or undistorted) image may be obtained by applying camera intrinsic parameters (such as lens radial or barrel distortion, sensor skew, etc.) to the raw image obtained from the image sensor 125.

Figure 2:
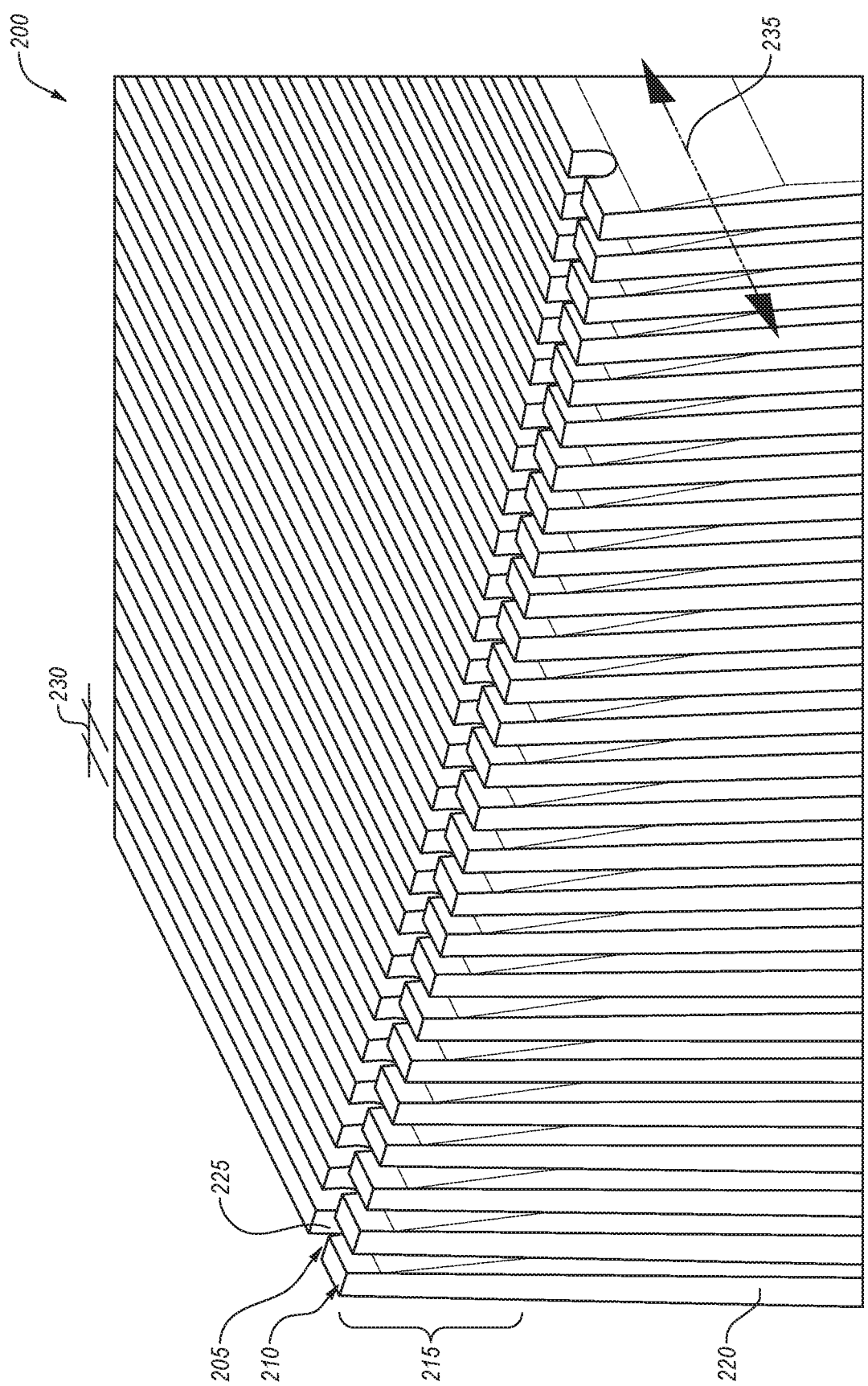
FIG. 2 illustrates a leaf bank of a multi-leaf collimator, in accordance with one embodiment.

In one embodiment, the MLC includes a pair of leaf banks, which may be referred to herein as a left bank and right bank for convenience. FIG. 2 illustrates details of the structure of one leaf bank 200 of collimation leaves, in accordance with one embodiment. As shown, in one embodiment each leaf includes a notch 225 in a top edge, the notch 225 having a leading edge 205. Each leaf additionally includes a top corner 210 and a front edge 220. The leaves may be sloped so that the leaves approximately touch at some vertical distance from a top edge of the leaves, but are separated by a gap 230 at the top edge. In other words, the width of each leaf narrows at the top to form a tongue 215. The gap 230 between the tongues of adjacent leaves is shown. Also shown is a linear direction of travel 235 of the leaves.

FIG. 3 illustrates a side view of a single collimation leaf 300, in accordance with one embodiment. A notch 325 is shown at a top and bottom of the collimation leaf 300. As also shown, the front edge 320 of the leaf extends out past the top leaf corner 310. Thus, the leaf 300 has a slope 330 from the front edge 320 to the top leaf corner 310. As a result, images generated by the image sensor 125 may show the top leaf corner 310 of leaves, but may not show the front edge 320 (e.g., if the front edge 320 is in shadow).

Figure 4A:
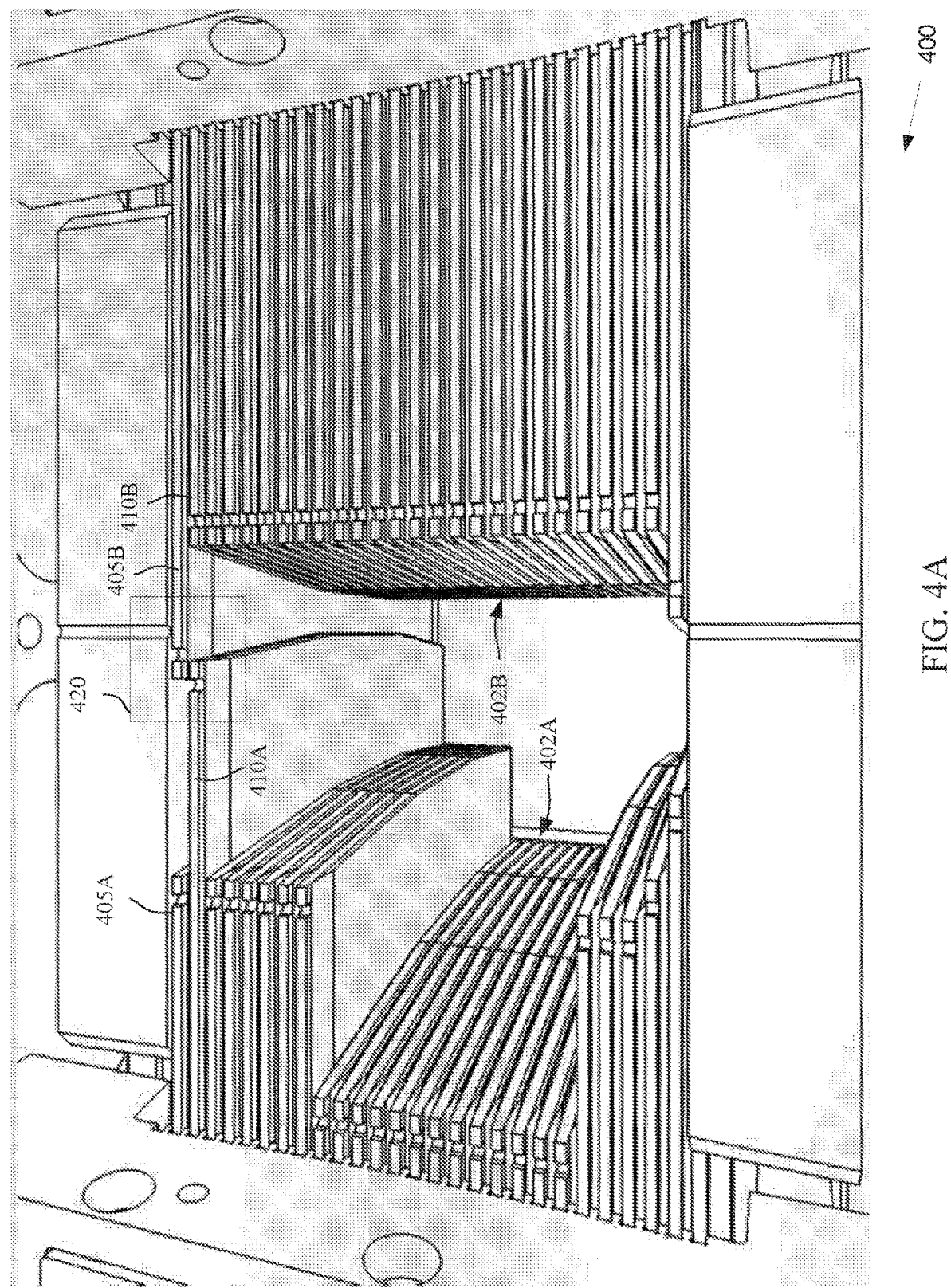
FIG. 4A illustrates an oblique-view image of an aperture for a multi-leaf collimator, in accordance with one embodiment.
Figure 4B:
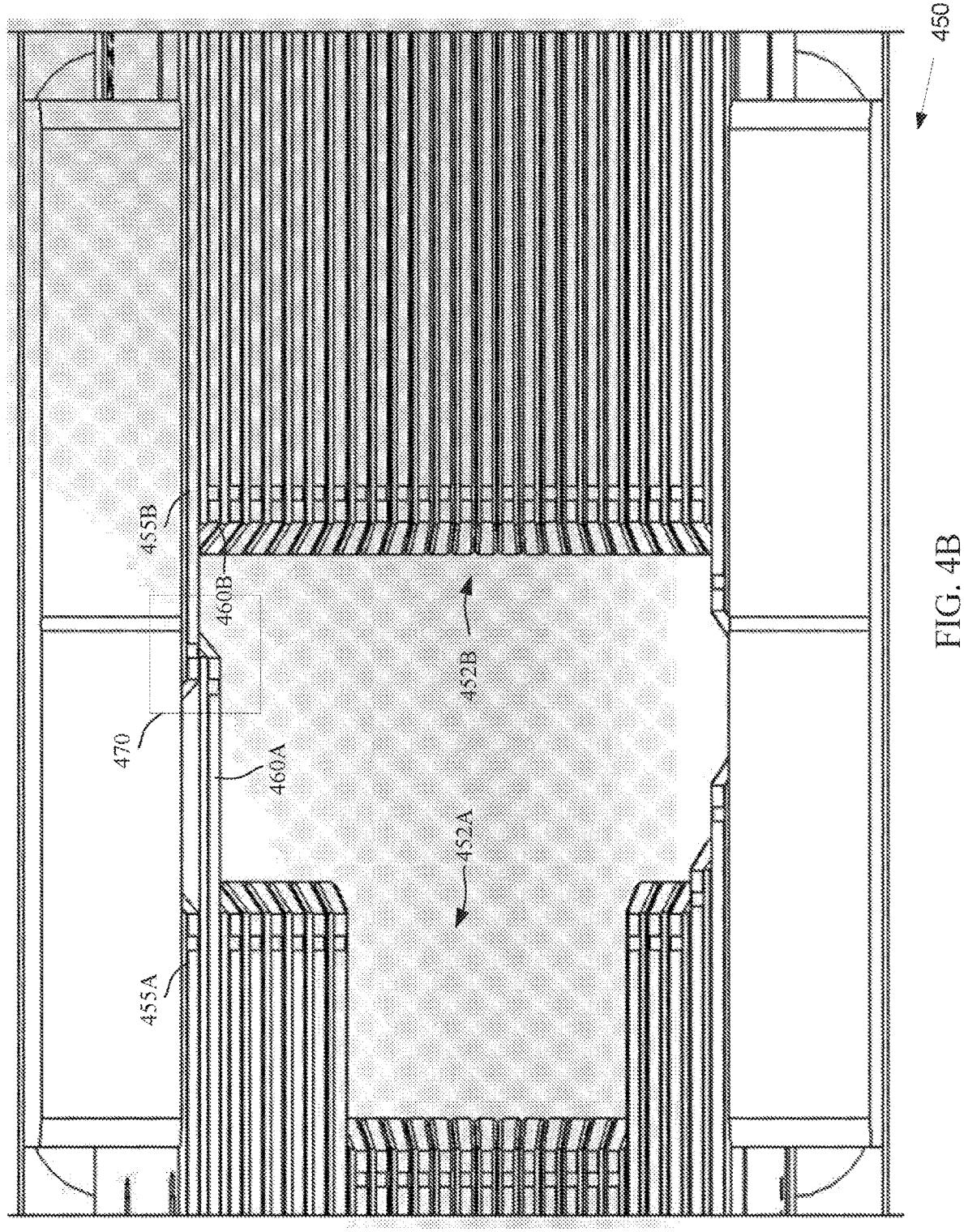
FIG. 4B illustrates a top-view pre-generated template image of an aperture for a multi-leaf collimator, in accordance with one embodiment.

As discussed above, the image sensor 125 is off center from the beam axis, and therefore generates oblique-view images of the MLC aperture. FIG. 4A illustrates an oblique-view image 400 of an example calibration aperture for a multi-leaf collimator, in accordance with one embodiment. FIG. 4B illustrates a top-view template image 450 of an example calibration aperture for a multi-leaf collimator, in accordance with one embodiment. The image-based aperture verification system may be calibrated by performing keypoint matching between the oblique-view image and the top-view template image in order to generate a perspective transformation matrix. Alternatively, the resulting transformation may not be represented in a matrix. Other types of transformation parameters may instead by computed and stored for transforming future images from the image sensor 125.

In one embodiment, the leaves in the calibration aperture are in non-uniform positions. The leaves in the calibration aperture may be positioned to cause the aperture to have numerous zigzags, which creates numerous edges and thus numerous keypoints. In other words, the leaves may be adjusted so that leaf tips (leading edges or ends) and notches do not line up but instead form a sequence of corners and troughs like the skyline of a city. In one embodiment, the leaves are arranged in a minimally non-repetitive pattern (e.g., a completely non-repetitive arrangement). In one embodiment, each adjacent leaf has a different position than the leaves that border it. The presence of edges and corners help create many unique patterns that are easily located and matched by standard feature descriptors. In one embodiment, the leaves are positioned in a semi-random fashion whereby the relative horizontal displacement between neighboring leaves is up to 4 times the distance in pixels between neighboring leaves, and one or more leaves are extended past the center of the collimator to help block external or ambient light from entering a housing of the MLC.

Figure 7A:
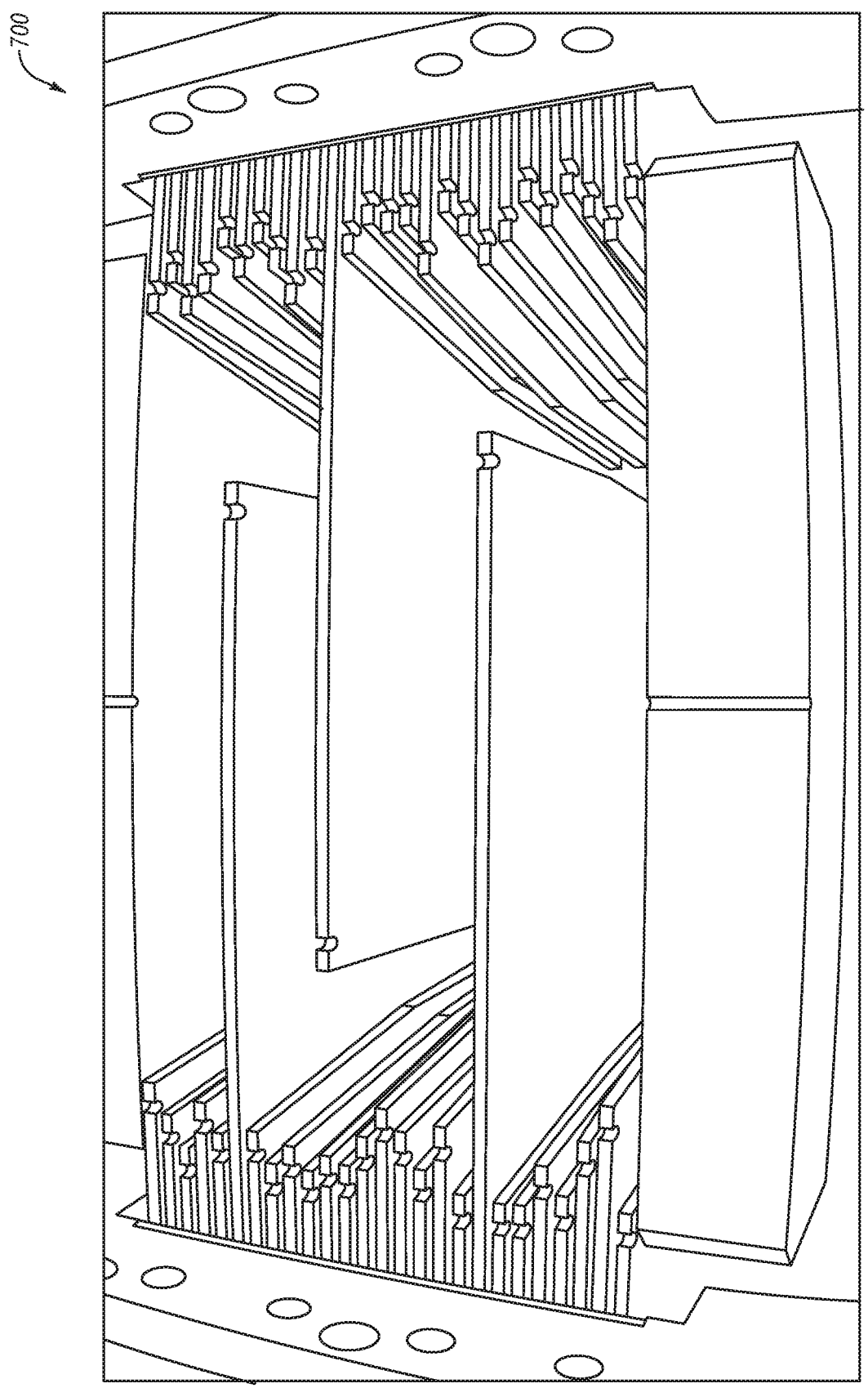
FIG. 7A illustrates a distorted oblique-view image of a calibration aperture for a multi-leaf collimator, in accordance with one embodiment.
Figure 7B:
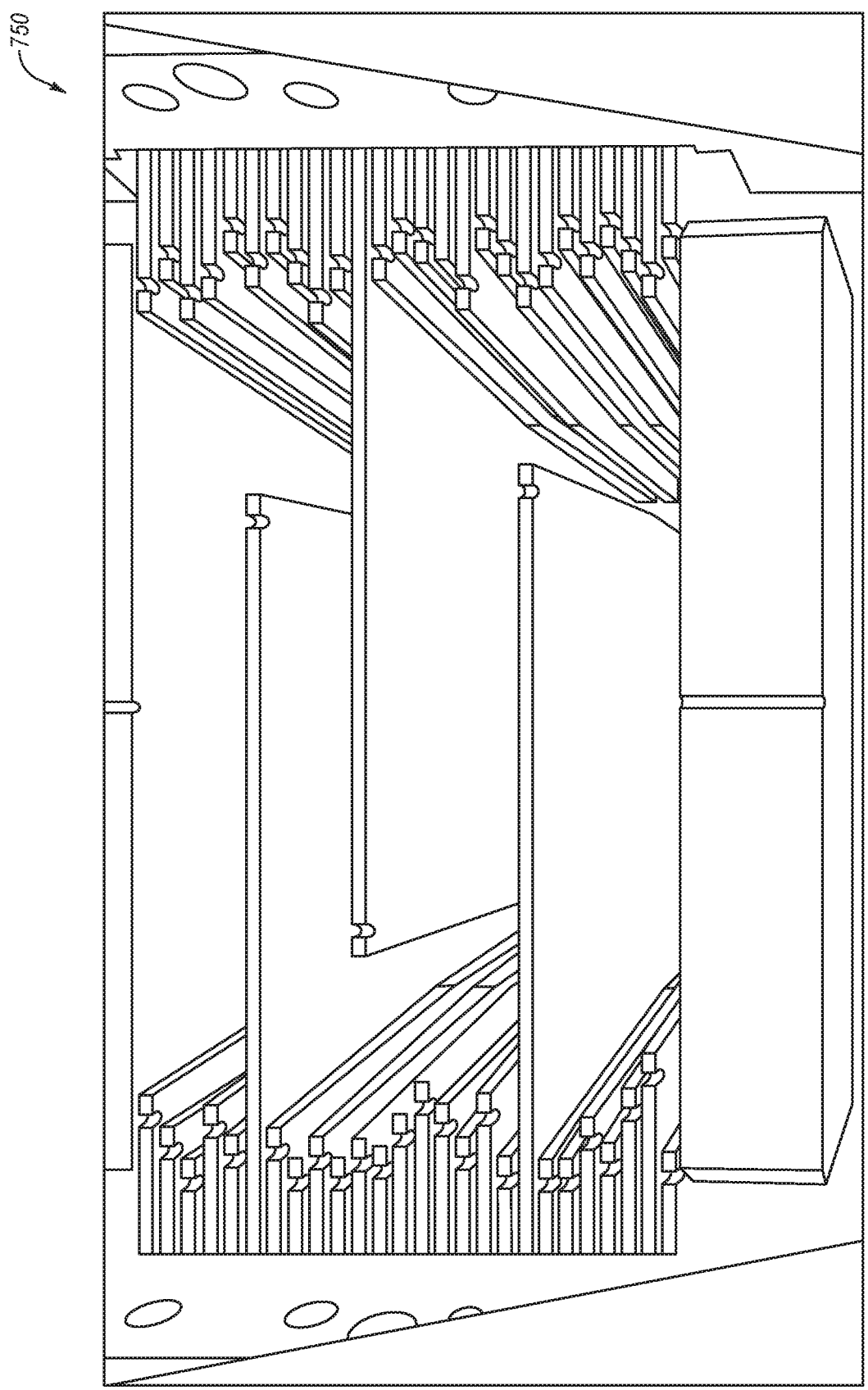
FIG. 7B illustrates a top-view image of the calibration aperture of FIG. 7A after a perspective transformation and optical correction, in accordance with one embodiment.

In one embodiment, the calibration aperture corresponds to the aperture shown in FIGS. 7A-7B. As shown, each adjacent leaf in the aperture has a different position. Additionally, some leaves in the aperture are extended past the beam axis of the MLC. This causes a screen that reduces ambient light in the MLC, which improves an accuracy of keypoint matching by reducing variation between the template image and images captured in different external lighting environments. In one embodiment, three leaves are extended to block ambient light. Alternatively, one, two or more leaves may be extended to block ambient light. Alternatively, calibration may be performed in a dark room or after mounting an opaque light cover on the distal end of the MLC, allowing all leaves to be opened.

Referring back to FIG. 4B, the image template may be a distortion-free synthetic image generated computationally using rendering (e.g., by rendering a computer-generated three dimensional model from an ideal image sensor viewpoint that is directly above the leaves and along the beam axis). An alternative solution would be to put the image sensor in the overhead position in a partially assembled engineering unit using a specialized mount for acquiring the template image. Alternatively, the image template may be a manually and/or computationally manipulated image that was originally generated by the image sensor. For example, an oblique-view image may be manipulated using control points constrained on a perspective transformation to generate the image template. In one embodiment, a perspective transformation is numerically solved given manually or automatically defined coordinate mappings (from distorted space to template space). For example, given seven or more points along the guide frames and side protection plates in an oblique-view image plus their ideal locations in the reference coordinate space (where they form a perfect rectangle), any standard homography estimation technique can be applied to compute a transformation matrix. This transformation matrix may then be applied to the oblique-view image to generate the image template. Note that embodiments described herein do not require a precise scale (pixel size) in the template image since a procedure for calibration of pixel position to actual leaf position in millimeters may be performed. A single template image may be created, and may be used by many different MLCs having similar leaf design and lighting system. This allows for a wide range of mechanical variation in the image sensor mounting hardware.

An appropriate image template is one in which the direction of travel of all leaves is horizontal, and for any given leaf translation the x-coordinate is the same for each leaf in the same bank. In other words, horizontally opposed leaf pairs will have the same y-coordinate (vertical pixel location) at any leaf translation, and each leaf in a given bank will have the same horizontal pixel location for the position at which the leaves exit a guide frame.

The image template, and other transformed top-view images, may have a reference coordinate space (RCS) that provides an image that is easily processed and x-y coordinates that are easily translated into a mechanical space (e.g., that measurements from displacement gauges can easily be transformed into). The reference coordinate space is a rectilinear and well defined coordinate space, in which assumptions about leaf appearance, leaf number and leaf travel direction can be made. One advantage of this approach is a reduced requirement for tight mechanical tolerances, resulting in significantly lower component and manufacturing costs. In the reference coordinate space, each leaf may move along only a single axis (e.g., along a single y coordinate).

In one embodiment, calibration is performed in order to accurately transform the oblique-view images of the image sensor 125 into top-view images. Calibration may be performed by positioning the leaves of the multi-leaf collimator to a specified calibration aperture and comparing to a template image. The specified calibration aperture may be a precise configuration that causes multiple keypoints.

Image processing is performed to determine keypoints in both the template image 450 and the oblique-view image 400. As shown, the oblique view image 400 includes a left leaf bank 402A and a right leaf bank 402B, each including the same number of leaves that have been arranged in specified positions that correspond to the same positions of the leaves for the left leaf bank 452A and the right leaf bank 452B in template image 450. In particular, in the illustrated example leaves 405A, 405B, 410A and 410B have positions that correspond to positions of leaves 455A, 455B, 460A and 460B.

Once the keypoints are determined in the two images 400 and 450, keypoint matching is performed to match the keypoints from the distorted oblique-view image 400 to corresponding keypoints in the template image 450. In one embodiment, a feature matching technique that is scale-invariant, rotation-invariant, and/or orientation-invariant is used to match keypoints. Examples of keypoint generation algorithms/descriptors that may be used includes scale-invariant feature transform (SIFT), generalized robust invariant feature (G-RIF), speeded up robust features (SURF), gradient location-orientation histogram (GLOH), binary robust invariant scalable keypoints (BRISK), fast retina keypoint (FREAK), oriented FAST and rotated BRIEF (ORB), and so on. An example of a feature matching algorithm that may be used to match the keypoints between the images 400, 450 includes random sample consensus (RANSAC). Given sufficient number of keypoint correspondences between the distorted oblique-view image and the template image, the mapping into the RCS may be obtained with high tolerance for mismatched keypoints by solving the inverse problem with random sample and consensus (RANSAC)-based or least median squares robust fitting method. Increased variety of patterns (at multiple scales) created by the calibration aperture improves confidence of keypoint matches. The quantity of patterns created in the calibration aperture, and thus number of keypoint matches, increased the robustness of the fitting method to incorrect matches, and decreases error of the solution.

Figure 5:
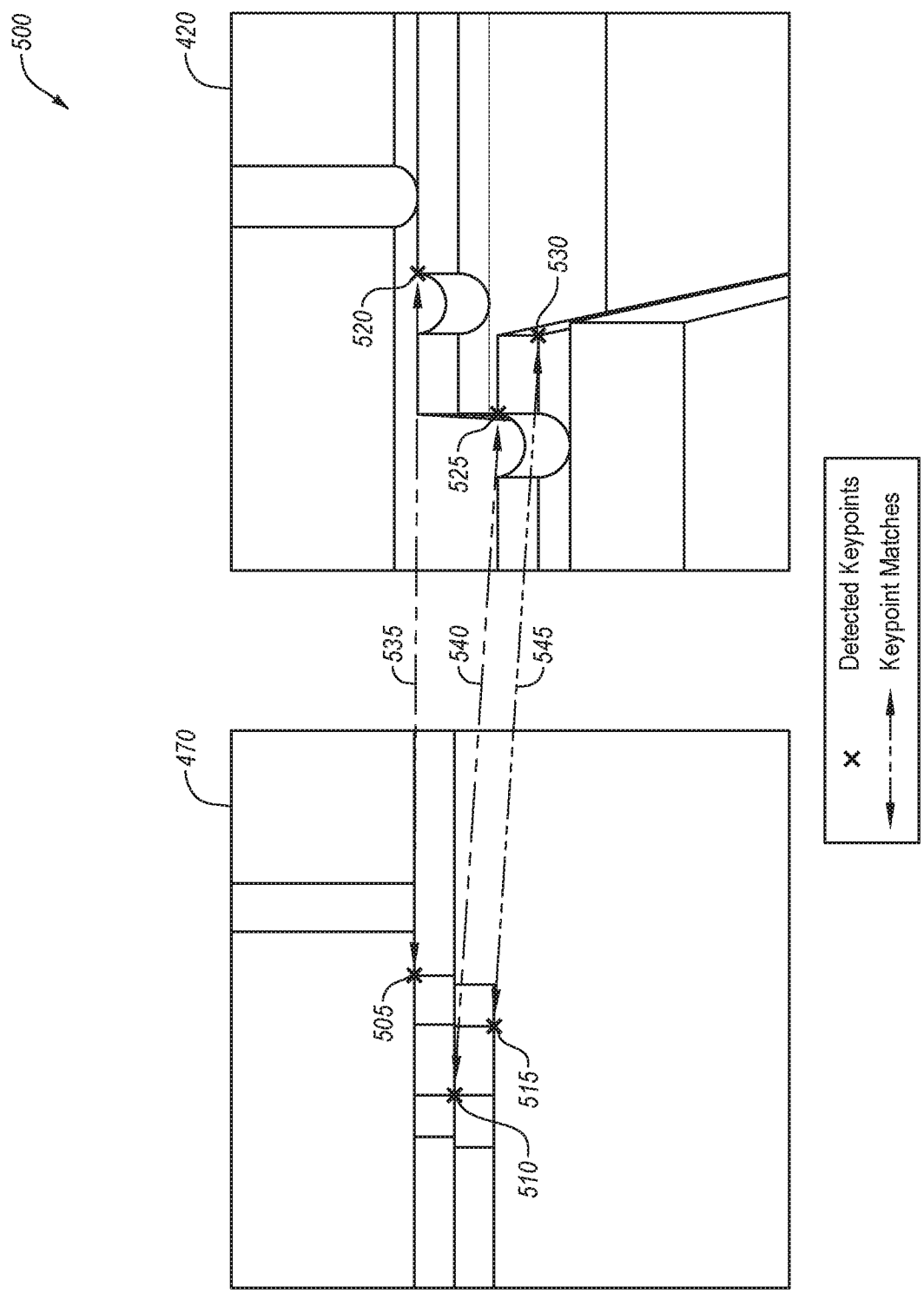
FIG. 5 illustrates keypoint matches between a region of a template image and a corresponding region of an oblique-view image of an MLC aperture, in accordance with one embodiment.

A window 420 of the oblique view image corresponds to a similar window 470 of the template image. FIG. 5 illustrates feature matching 500 between regions of zoomed in views of the windows 420 and 470. Detected keypoints 505, 510, 515 are shown in window 470, and detected keypoints 520, 525, 530 are shown in window 420. Keypoint matches 535, 540, 545 are shown that match keypoint 505 to keypoint 520, that match keypoint 510 to keypoint 525, and that match keypoint 515 to keypoint 530.

FIG. 6 illustrates a contrived example zoomed in view of keypoint match 600 for a single keypoint 625, 630 between the template image 605 and the oblique-view image 610. Keypoint region 615 is shown to include keypoint 625, and keypoint region 620 is shown to include keypoint 630. A keypoint match 635 is shown between keypoint 625 and keypoint 630. An output of the keypoint matching algorithm may be a transformation matrix that may be used to transform oblique-view images taken by image sensor 125 into top-view images having the reference coordinate space.

Calibration may also include calibrating a correspondence between the image-based aperture verification system and an additional aperture verification system (e.g., a primary aperture verification system). One way to calibrate pixel position to actual leaf position is to follow a calibration procedure, which moves leaves in known spatial increments (using encoders), and calibrating the distance traveled by the leaf to the distance traveled as observed on the image-based aperture verification system. Once performed for each leaf, a conversion between encoder counts (or mm of leaf travel) and pixels can be estimated for each leaf.

FIG. 7A illustrates an oblique-view image 700 of a calibration aperture for the MLC, in accordance with one embodiment. FIG. 7B illustrates a top-view image 750 of the calibration aperture generated by performing a perspective transformation of the oblique-view image 700, in accordance with one embodiment. Similar perspective transformations may be performed for any MLC aperture. In order to simplify image processing of an image to determine an MLC aperture, the oblique-view image 700 may be transformed into the top-view image 750. The oblique-view image 700 may be transformed into the top-view image by applying a transformation matrix to the oblique-view image 700. The transformation matrix may be generated by performing calibration of the image based aperture verification system, as described above with reference to FIGS. 4A-6. Once the transformation matrix is created, the transformation matrix may be applied to each oblique view image generated by image sensor 125 to transform that image into a top-view image having a reference coordinate space. Image processing may then be performed on the top-view image to determine leaf positions.

Once the oblique-view image 700 is transformed into the top-view image 750 having the reference coordinate space (also referred to as a reference coordinate system), the image can be broken into subdomains, where each subdomain corresponds to a single leaf. Image processing can then be performed within each subdomain to determine a leaf position of the leaf corresponding to that subdomain. In one embodiment, notches on the leaves are used as a proxy for leaf leading edge positions because the leading edge positions may not be visible. In other embodiments, one may use a proxy other than a notch. Any visual feature on the camera-facing side of the leaf can be used for tracking the leading edge of the leaf. Examples of other features that may be used as a proxy include colored beads affixed to the leaves, etched patterns in the leaves, etc.

In one embodiment, template matching is performed within each subdomain to look for the location with the highest normalized cross-correlation coefficient between an image block within the subdomain and a set of MLC leaf notch templates. Each MLC leaf notch template may be an image template of a particular leaf notch. The leaf notch may be used as a surrogate for the position of the leading edge of the leaf, because the actual tip of the leaf (as shown in FIGS. 2-3) is not visible on the camera. Leaf edges are detected with one or more leaf edge templates, which are defined as sub-images representing the appearance of the tip of a leaf as seen from a camera. A leaf edge template has a vertical size approximately twice the width of a leaf and a horizontal size approximately four times the vertical size. The leaf edge templates in this case include the tip of the leaf and some space extending beyond the tip, the notch on the leaf, and a portion of the leaf extending beyond the notch toward the guide frame. The position of the side of the notch closest to the leaf tip is known in each leaf edge template. Accordingly, when a matching region in the image is determined, the location of the edge of the leaf, which is not visible on the image sensor, is also known via the mechanical design of the leaf as shown in FIGS. 2-3. This approach may be facilitated by precisely manufacturing the notch with a tight tolerance on its position with respect to the leading edge (end) of the leaf. When the notch is detected, the delta/or offset between the notch and the end of the leaf may be factored in to accurately determine a position of the end of the leaf.

The confidence measure for leaf detection may correspond to the confidence that objects used for detecting the leaf position in the image have been correctly identified. This may be done by computing a normalized correlation coefficient (NCC) for the matched leaf template and the corresponding sub-region of the top-view image centered about the notch on the leaf. In one embodiment, one or more leaf notch templates are moved along a subdomain of the top view image to identify a location with the highest NCC, which is likely the location of the notch. In one embodiment, multiple notch templates are used to improve robustness (e.g., by changing illumination and view angle that's dependent on the position of the leaf). The NCC is a modification of the standard cross-correlation measure where the standard cross-correlation includes subtracting the means and dividing by the standard deviation of the sub-region, making this metric more suitable to image processing applications in which brightness of the image can vary due to lighting and exposure conditions. The NCC values are floating point numbers, ranging from 0 to 1. An absolute value of 1.0 corresponds to an exact match (after mean and standard deviation normalization) between the image template and the sub-region of the distorted oblique-view image, while a value of 0 corresponds to no correlation. In one embodiment, a value of 0.6 is used as the threshold for determining acceptable detection confidence. For the grayscale intensities of a region of the distorted oblique-view image, u, and the matching leaf edge template, v, an NCC value is computed as:

$$n = \frac{\sum_{p,q}(u)p, q\bigg) - \overline{u}\bigg)(v(p, q) - \overline{v})}{\sqrt{\sum_{p,q}((u)p, q) - \overline{u})^2} \sqrt{\sum_{p,q}((v)p, q) - \overline{v})^2}}$$

Where p and q are the row and column indexes of the pixels spanned by the leaf notch/edge template (and by the region of the distorted oblique-view image detected as corresponding to the leaf notch). Other measures or even leaf tracking algorithms may be applied to determine the position of the leaf from images acquired from the camera sensor.

Figure 8:
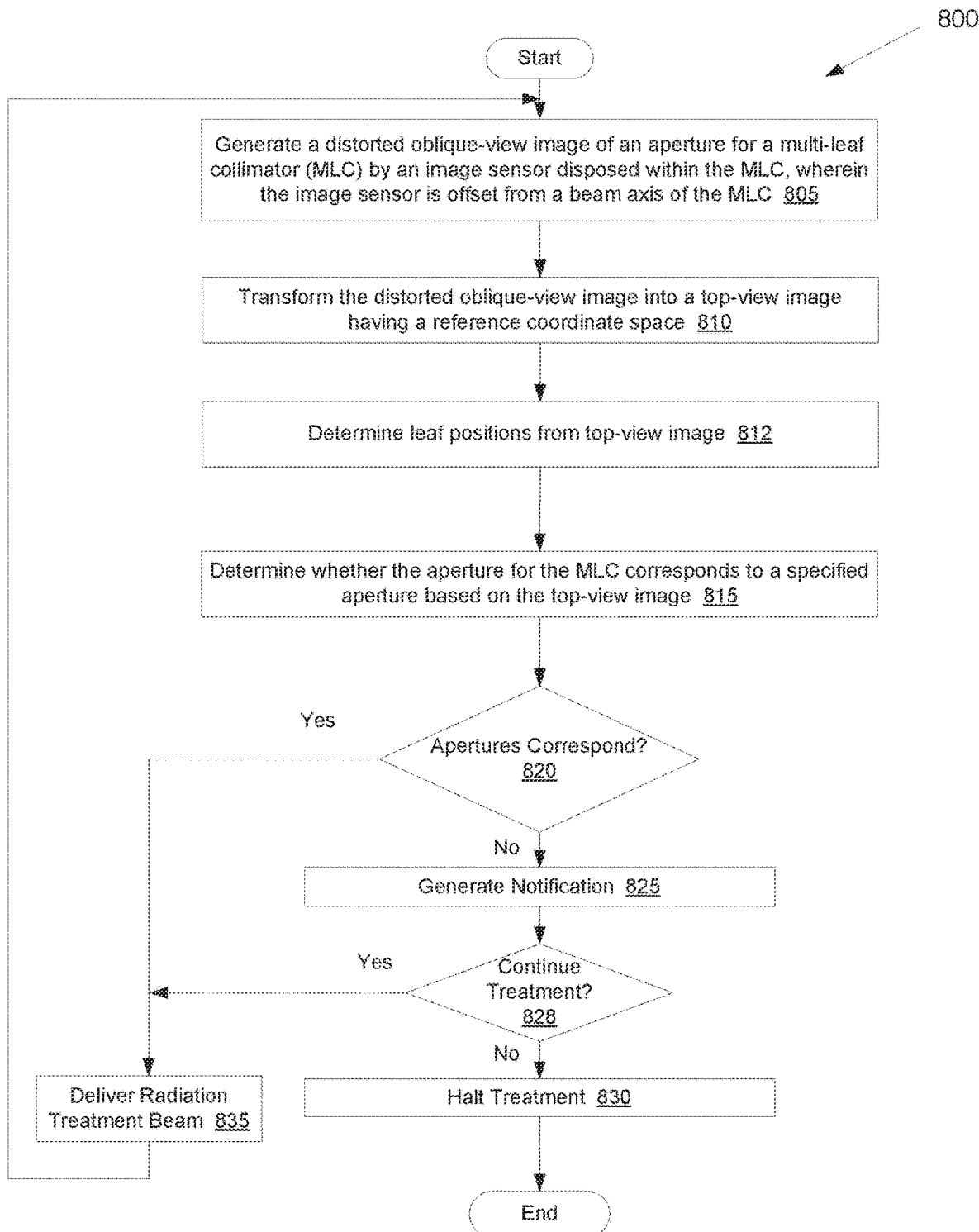
FIG. 8 illustrates one embodiment for a method of transforming an oblique-view image of an aperture for an MLC into a top-view image.

FIG. 8 illustrates one embodiment for a method 800 of transforming an oblique-view image of an aperture for an MLC into a top-view image. Operations of method 800 may be performed by an image-based aperture verification system, which may include an image sensor and a processing logic that processes data from the image sensor. The processing logic may include firmware, software, hardware, or a combination thereof. For example, the processing logic may include a processor executing one or more image processing algorithms.

At block 805, an image sensor disposed within an MLC generates a distorted oblique-view image of an aperture for the MLC. The image sensor may be disposed at a location in the MLC that is offset from a beam axis of the MLC, and may generate images of a top face of multiple leaves that form the aperture. At block 810, processing logic transforms the distorted oblique-view image into a non-distorted top-view image having a reference coordinate space. This may be performed in a sequence of transformations. A first transformation may remove lens distortion, and may transform the distorted oblique-view image into a non-distorted oblique-view image. The second transformation may be a perspective transformation that transforms the non-distorted oblique-view image into a non-distorted top-view image. The second transformation may be performed by applying a perspective transformation matrix (e.g., projective or homography) or other transformation parameters to the oblique-view image. At block 812, image processing is performed to determine leaf positions of each leaf of the MLC using the top-view image.

At block 815, processing logic determines whether the aperture for the MLC corresponds to the specified aperture based on the top-view image. In one embodiment, processing logic compares the determined leaf positions to leaf positions specified in a treatment plan to determine a variation between determined leaf position and the specified leaf position. In another embodiment, processing logic compares the determined leaf positions to leaf positions determined by an additional aperture verification system (e.g., the leaf displacement gauges). If the leaf positions computed by the image-based aperture verification system vary from the leaf positions computed by the additional aperture verification system by less than a threshold amount, then the leaf positions are considered to match. At block 820, if the apertures correspond, the method continues to block 835. If the apertures do not correspond, the method proceeds to block 825. At block 825, processing logic generates a notification. At block 828, a user determines whether to continue or to halt treatment. If the user determines to continue, the method continues to block 835. If the user determines to halt treatment, the method continues to block 830. At block 830, processing logic may then halt treatment. If the leaf positions correspond, then the measured aperture corresponds to a specified aperture in the treatment plan and/or to an aperture as measured by an additional aperture verification system. At block 835, processing logic may then cause a linear accelerator to deliver a radiation treatment beam. The method may then return to block 805 so that additional treatment beams may be delivered. If all treatment beams have been delivered, the method may end.

Figure 9:
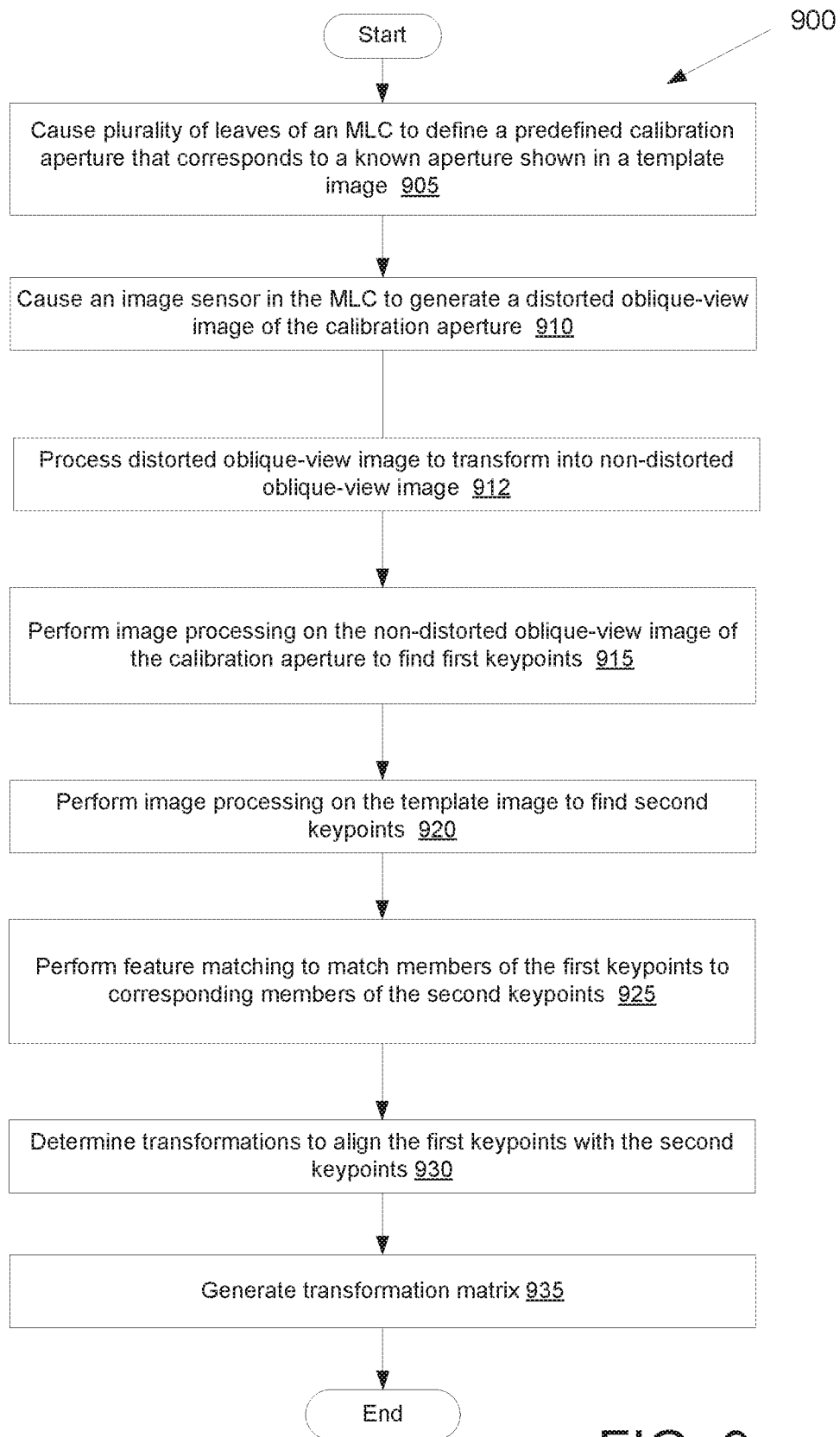
FIG. 9 illustrates one embodiment for a method of calibrating an image-based aperture verification system.

FIG. 9 illustrates one embodiment for a method 900 of calibrating an image-based aperture verification system. Operations of method 900 may be performed by an image-based aperture verification system, which may include an image sensor and a processing logic that processes data from the image sensor. Operations may also be performed by processing logic that controls an MLC and/or a radiation treatment device. The processing logic may include firmware, software, hardware, or a combination thereof. For example, the processing logic may include a processor executing one or more image processing algorithms.

At block 905 of method 900, processing logic causes leaves of an MLC to be positioned so that they define a predefined calibration aperture that corresponds to a known aperture shown in a template image. At block 910, processing logic causes an image sensor of the MLC to generate a distorted oblique-view image of the calibration aperture. At block 912, processing logic processes the distorted oblique-view image to transform it into a non-distorted oblique-view image. The term "non-distorted" refers to lack of optical distortion (caused by a lens or camera) rather than geometric distortion caused by the oblique view angle. At block 915, processing logic performs image processing on the non-distorted oblique-view image of the calibration aperture to find a first set of keypoints. At block 920, processing logic performs image processing on the template image to find a second set of keypoints. In one embodiment, the template image is a top view (also referred to as overhead view) image that corresponds to a camera that is along the beam axis and pointing in the direction of the beam axis. At block 925, processing logic performs feature matching to match members of the first set of keypoints to corresponding members of the second set of keypoints. At block 930, processing logic defines transformations that align the first set of keypoints to the matching second set of keypoints. At block 935, processing logic generates a transformation matrix (or set of transformation parameters) using the matched keypoints.

In embodiments, multiple pieces of information may be spatially and temporally registered, and then presented to a user in a unified presentation. Use of the controlled reference coordinate space enables information to be overlaid over non-distorted top-view images of the MLC aperture. Since all of the information is mapped to the reference coordinate space (RCS), it is straightforward to then overlay each of these items of information over the non-distorted top-view image that also has the RCS. Each item of information may be assigned a layer, which may be turned on or off based on user command. Examples of types of information that may be assigned a layer and displayed as an overlay on the non-distorted image include a digitally reconstructed radiograph (DRR) generated based on pre-treatment computed tomography (CT) images, leaf positions as determined by an aperture verification system, leaf positions dictated by a treatment plan, and so on. Other information that may be shown in an overlay includes contours from a treatment plan (e.g., organs at risk (OAR)), a projection of dose distribution as defined by the treatment plan, etc. Potentially any information that is available from treatment planning may be shown to increase confidence and provide a better sense of where the radiation beam is pointing in the context of the previously generated treatment plan. Thus, a view of the MLC aperture may show where leaves should be as well as where the leaves are currently positioned. This information may be shown in a time-synchronized movie mode (e.g., in real time or pseudo-real time) or as static snapshots (e.g., before and after delivery of a radiation treatment beam). Different visual indications may be used to show various types of information. For example, color and/or shading may be used to show leaves that are moving, leaves for which there is a disagreement between the image sensor based aperture verification system and another aperture verification system, leaves for which the current positions differ from those of a treatment plan, and so on.

In one embodiment, the image-based aperture verification system provides a continuous stream of image data, which is continuously analyzed to estimate real-time leaf positions. The optically estimated leaf positions may additionally be continuously compared with both leaf positions as determined by an additional aperture verification system and leaf positions specified in the treatment plan to ensure safe and accurate treatment beam collimation. The presentation of the non-distorted images also provides an additional layer of quality assurance, in that a user may visually see the current aperture to determine if the aperture is correct. This may increase user confidence and may provide valuable system insight in case of system malfunction. For example, if there is disagreement between leaf positions between the aperture verification systems, a user may differentiate between mechanical and optical failures based on a review of the image.

Figure 10:
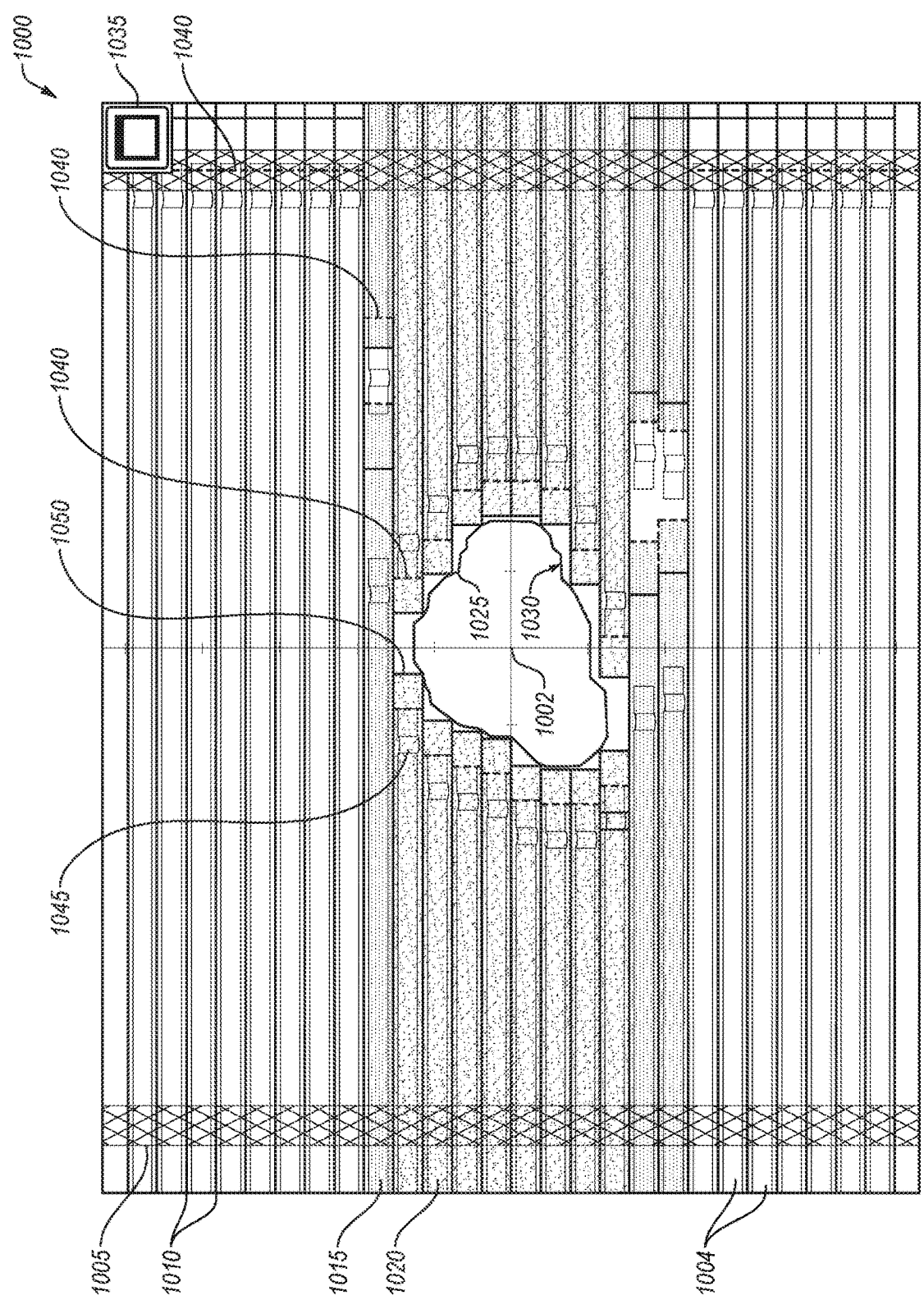
FIG. 10 illustrates a pictorial representation of an MLC aperture overlaid on a top-view image of the MLC aperture, in accordance with embodiments described herein.
Figure 11:
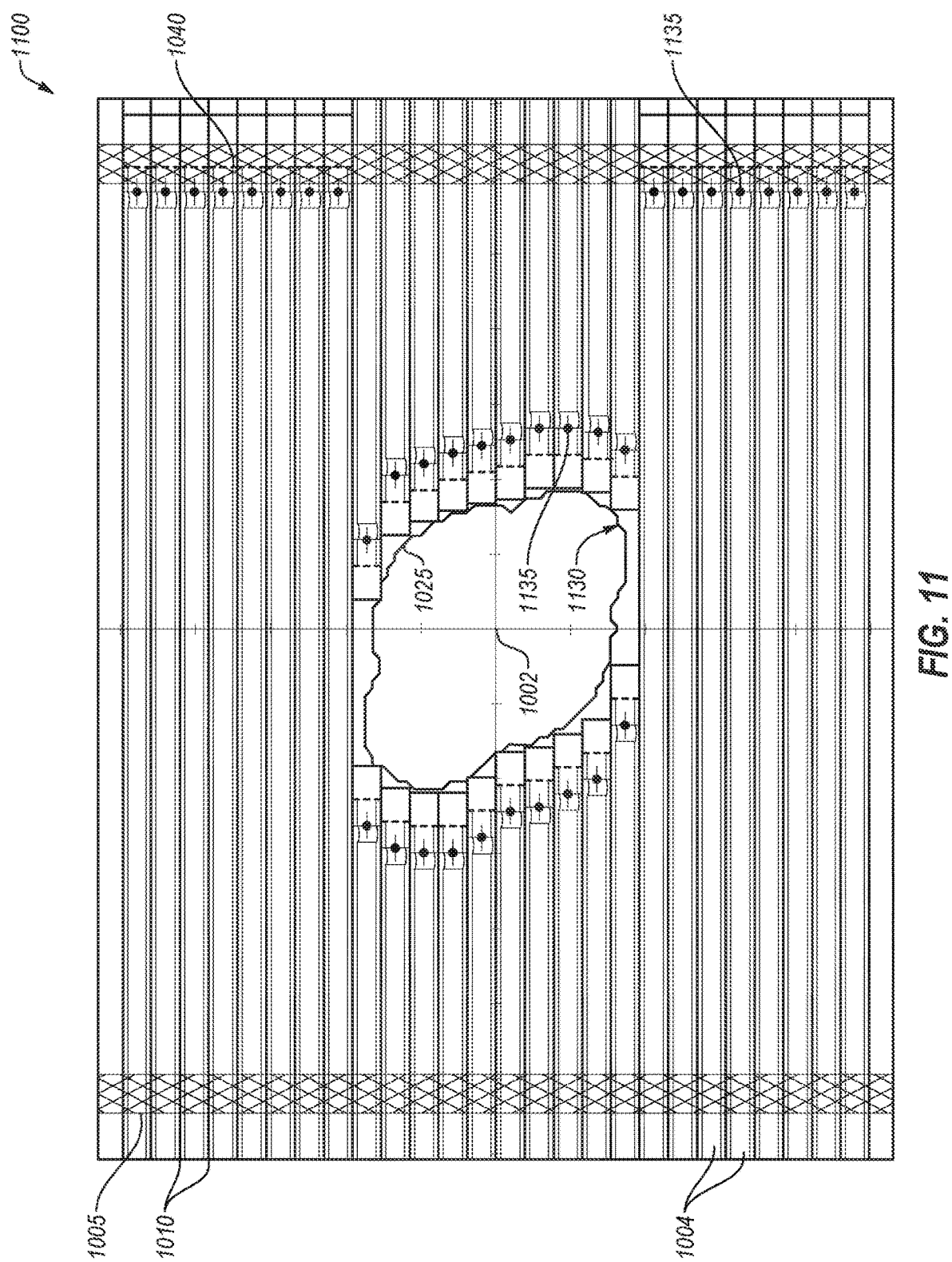
FIG. 11 illustrates an additional pictorial representation of an MLC aperture overlaid on a top-view image of the MLC aperture, in accordance with embodiments described herein.
Figure 12:
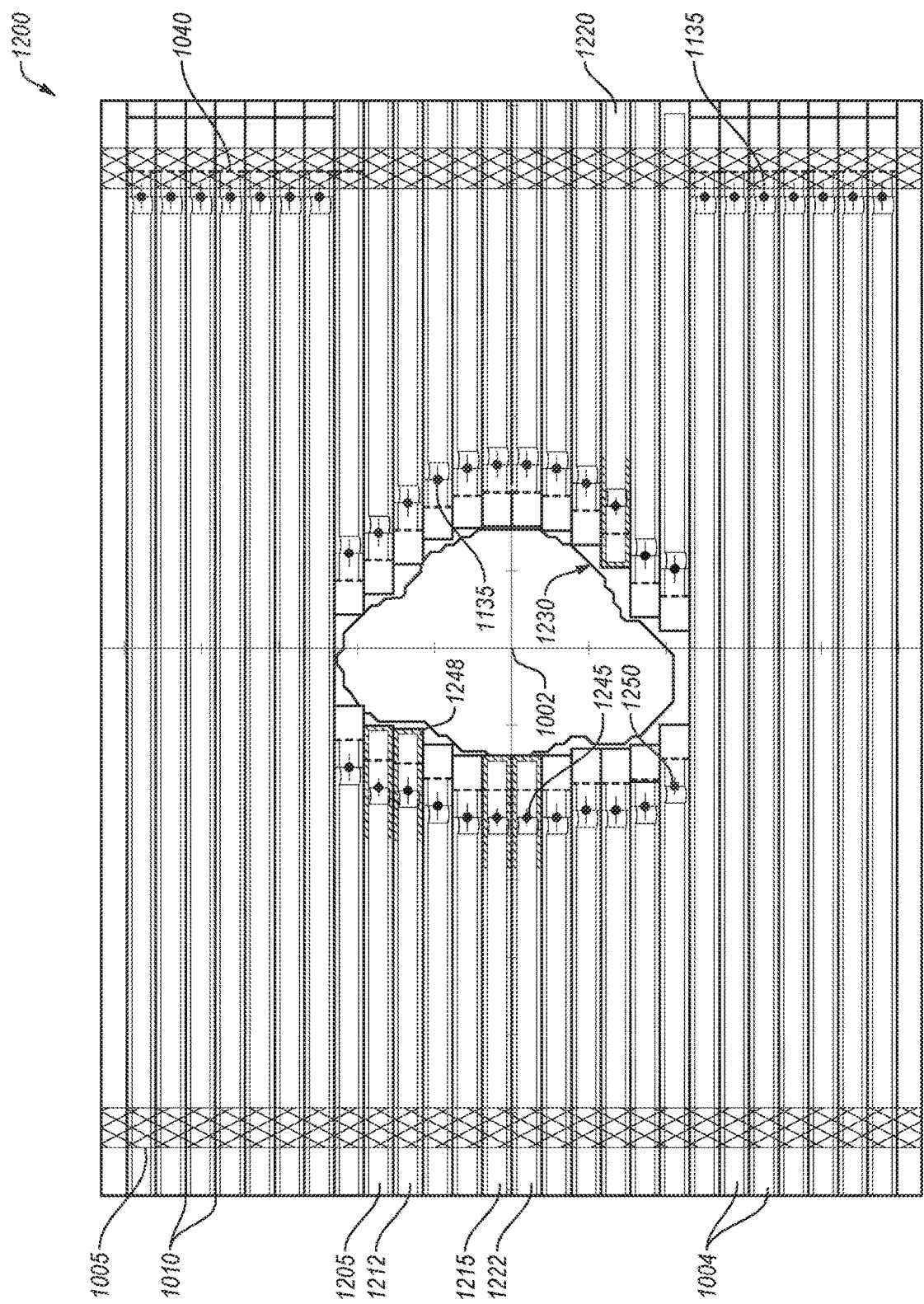
FIG. 12 illustrates another pictorial representation of an MLC aperture overlaid on a top-view image of the MLC aperture, in accordance with embodiments described herein.

FIGS. 10-12 illustrate pictorial representations of an MLC aperture, in accordance with embodiments described herein. Referring to FIG. 10, diagram 1000 shows a top-view image of an MLC aperture 1030 with multiple overlays. Similarly, in FIG. 11 diagram 1100 shows a top-view image of an MLC aperture 1130 with multiple overlays, and in FIG. 12 diagram 1200 shows a top-view image of an MLC aperture 1230. The top-view image may have been generated as descried with reference to FIG. 8 in embodiments.

In each of the diagrams 1000, 1100, 1200, a center 1002 of the diagram may correspond to a beam axis normal to the diagram. The diagrams may show a live video camera image, a static image, and/or superimposed graphics that give real-time information about the MLC leaf positions. In one embodiment, diagram 1000 shows a live video camera image (e.g., when a treatment radiation beam is off) and diagram 1100 shows a static camera image (e.g., when the treatment radiation beam is on, when the treatment radiation beam is about to begin, or following delivery of the treatment radiation beam) of leaves 1004. In one embodiment, selecting a maximize button 1035 causes a window with secondary feedback details to open.

In the illustrated diagrams 1000, 1100, 1200, a patient shield 1005 are represented by vertical bars with crosshatch. The patient shield 1005 may be over the left and right banks of MLC leaves. An overlay of lines and rectangles 1010 having a first visual property (e.g., a first color or solid line with a first line weight) may show leaf positions as measured by a first aperture verification system (e.g., by an encoder). In one embodiment, blue lines/rectangles are used to show leaf positions as measured by the first aperture verification system. Rectangles 1010 surrounding each leaf may extend out from each bank to show the position of each leaf according to an MLC motor control system. The MLC motor control system may include a separate encoder or other displacement gauge for each individual leaf. The rectangles 1010 end at the front-most edge of each leaf, which may be in shadow in the top-view image (and thus not be visible in the top-view image). The front-most end or tip of the leaves may not be visible in the top-view image because the leaves may be tapered at their ends.

Vertical lines 1040 having a second visual property (e.g., a second color or dashed lines) may show a visible edge of each leaf. In one embodiment, green lines are used to show visible edges of leaves. The front-most edge 1050 of each leaf 1004 may be a known distance from the visible edge 1040 that is shown. In one embodiment, each leaf 1004 has a notch 1045 that is a known distance from a tip or end of the leaf. A position of the tip or end of the leaf 1004 may be determined by adding the known distance to the measured position of the notch 1045 for the leaf 1004.

A planning target volume (PTV) contour 1025 and/or other contours (e.g., of a tumor) contained within a treatment plan (e.g., OARs) may also be shown in the diagrams 1000, 1100, 1200. In one embodiment, the PTV contour 1025 is red. In one embodiment, the PTV contour 1025 is a solid line when the MLC leaves 1004 have reached their final positions (and are no longer moving) and a dashed line when the MLC leaves 1004 are in motion (and have not reached their final positions).

Diagram 1000 shows a video image (also referred to as a live image and movie image) as the image is generated. The image may be a moving image that is updated in real time or near-real time. In one embodiment, the image is updated at a rate of one frame (one image) every four seconds. Other refresh rates may also be used, such as 1 frame per second, 4 frames per second, 1 frame every 2 seconds, and so on. Such video images may include additional visual indications 1015, 1020 showing leaf movement. A first visual indication (e.g., a first shading) 1015 may indicate standard leaf movement, and a second visual indication (e.g., a second shading) 1020 may indicate that a moving leaf is approaching its final position. In one embodiment, gray shading is used for a leaf to indicate leaf movement of that leaf. In one embodiment, a shading for a visual overlay of a leaf changes briefly to yellow as the leaf approaches its final destination.

In one embodiment, while the leaves 1004 are moving, data from the image-based aperture verification system and the other aperture verification system may be in conflict. However, once the leaves 1004 reach their programmed positions, the data from these disparate systems should correspond. In another embodiment, the different aperture verification systems are time synchronized so that their data corresponds even as the leaves 1004 are moving.

Diagram 1100 shows a static image of an MLC aperture 1130. Detection results may be shown via detection markers 1135. In one embodiment, detection markers 1135 are shown as a plus sign superimposed on a small square, circle, diamond, or other shape. There may be one detection marker per leaf, which may be located at a leading edge of the leaf notch in some embodiments. The detection markers 1135 may be shown after a leaf position verification is performed (e.g., by comparing leaf position as measured one or more aperture verification systems). Each detection marker 1135 may be shown with a visual indication that shows a result of the leaf position verification for the associated leaf 1004. In one embodiment, the color of each detection marker indicates the detection confidence for the leaf detection algorithm of the image-based aperture verification system. Alternatively, or additionally, a shape of the detection marker 1135 may indicate detection confidence. Green and/or a circle may be used to indicate a confidence of 80-100% in one embodiment. Yellow and/or a square may be used to indicate a confidence of 60-80% in one embodiment. Red and/or a diamond may be used to indicate a confidence of less than 60% in one embodiment. In one embodiment, clicking and holding anywhere along a leaf 1004 causes the confidence value for that leaf to be shown with additional information including a numerical identifier for the leaf along its bank, the position of the leaf, and the percentage confidence value for that leaf.

When the detection confidence falls below a certain threshold, the image-based aperture verification system fails, and a soft stop may occur. Additionally, an additional details window may open with more details and instructions.

Diagram 1200 of FIG. 12 shows a static image of another MLC aperture 1230 after a verification failure of the image-based aperture verification system. In one embodiment, diagram 1200 is an example of an additional details window. As shown, in diagram 1200 leaves 1205, 1212, 1215, 1220 and 1222 have detection markers 1245 that indicate a failed verification by the image-based aperture verification system (e.g., red detection markers or detection markers with a diamond shape). In one embodiment, some detection markers 1250 may be shown in yellow or with a square shape to indicate that a confidence for associated leaves is at or above a first threshold (e.g., 60%) but below a second threshold (e.g., 80%). In one embodiment, some detection markers 1235 may be shown in green or with a circle shape to indicate that a confidence for associated leaves is at or above the second threshold (e.g., 80%). Each of leaves 1205, 1212, 1215, 1220 and 1222 are shown with a visual indication of a leaf alert border 1248 to call a user's attention to these leaves. In one embodiment, the leaf alert border 1248 is shown in yellow or orange or with a hashing as shown. A user may review the information for the failed leaves, and determine how to proceed. After a soft stop, a user may elect to continue treatment or abort treatment.

Figure 13A:
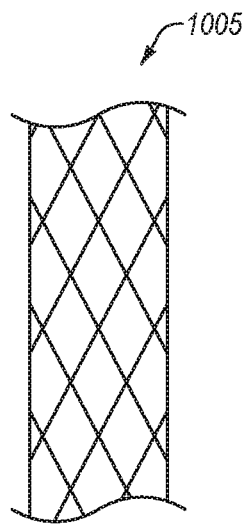
FIG. 13A illustrates a visual indication of a patient plane shield, in accordance with one embodiment.
Figure 13B:
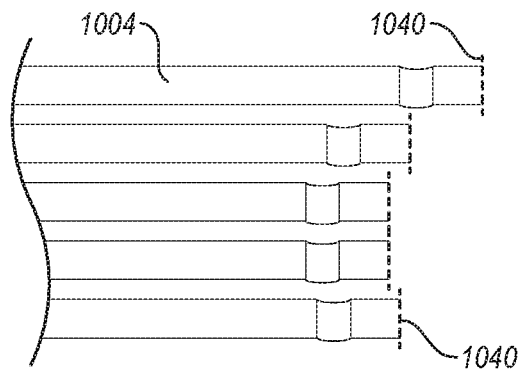
FIG. 13B illustrates a visual indication of a visible edge of a leaf in an MLC, in accordance with one embodiment.
Figure 13C:
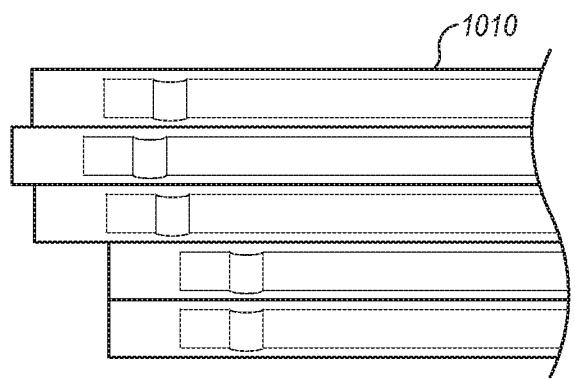
FIG. 13C illustrates a pictorial representation of a leaf of an MLC based on an aperture verification system, in accordance with one embodiment.
Figure 13D:
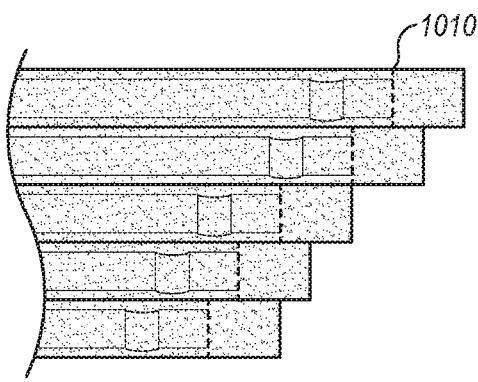
FIG. 13D illustrates a visual indication of moving leaves that are approaching a target position, in accordance with one embodiment.
Figure 13E:
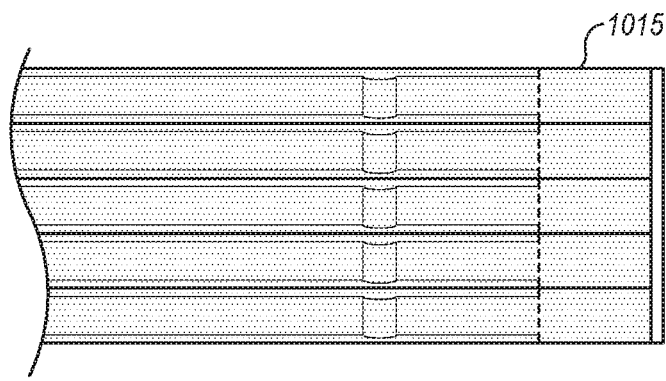
FIG. 13E illustrates a visual indication of moving leaves, in accordance with one embodiment.
Figure 13F:
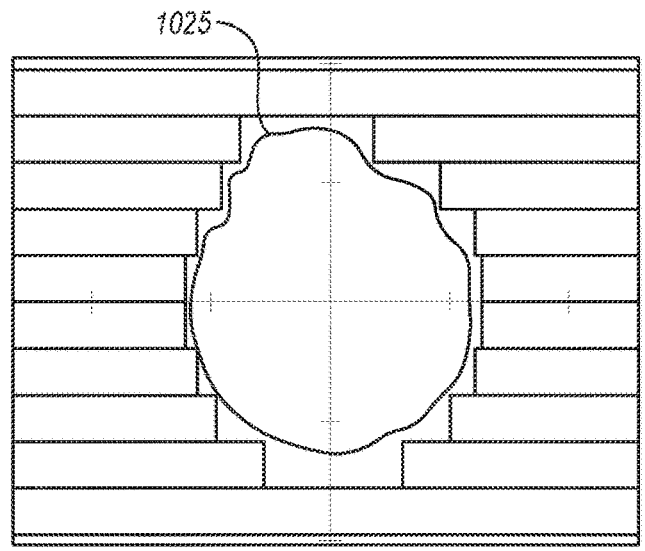
FIG. 13F illustrates a visual indication of a solid tumor contour, in accordance with one embodiment.
Figure 13G:
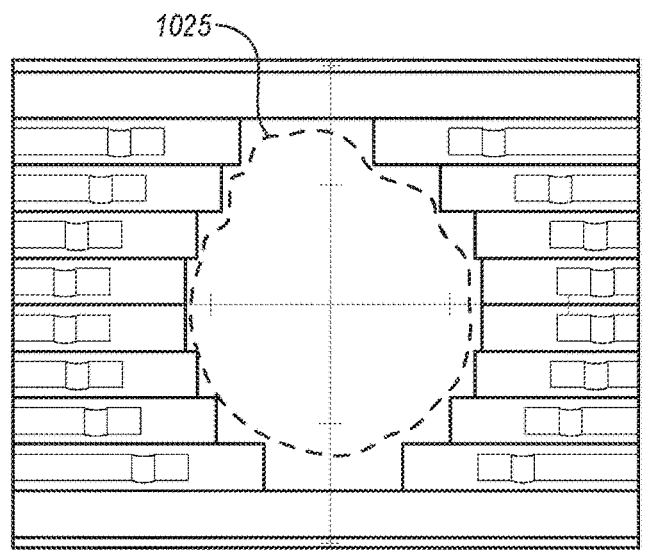
FIG. 13G illustrates a visual indication of a dashed tumor contour, in accordance with one embodiment.
Figure 13H:
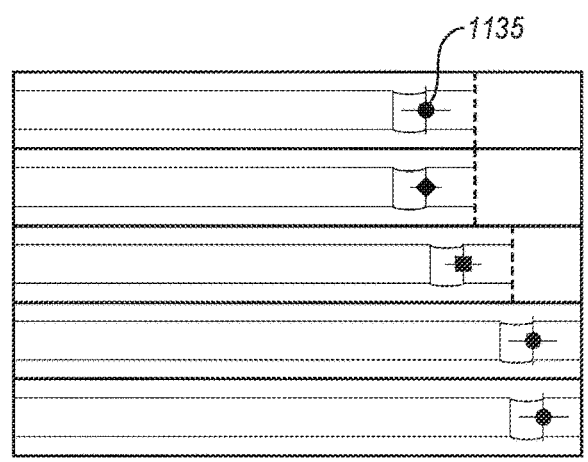
FIG. 13H illustrates a visual indication of detection markers, in accordance with one embodiment.

FIGS. 13A-13H illustrate visual indications for various attributes of the pictorial representations shown in FIGS. 10-12. FIG. 13A shows the patient plane shield 1005. FIG. 13B shows the vertical lines 1040 representing the visible edge of a leaf 1004. FIG. 13C shows a leaf outline 1010 as measured by an aperture verification system other than the image-based aperture verification system (e.g., a primary aperture verification system if the image-based aperture verification system is a secondary aperture verification system). FIG. 13D shows highlights 1020 of moving leaves approaching their target positions. FIG. 13E shows highlights 1015 of moving leaves. FIG. 13F shows a solid tumor contour 1025, indicating that the leaves are not moving and that a radiation beam can be delivered. FIG. 13G shows a dashed tumor contour 1025, indicating that the leaves are moving and that a radiation beam should not be delivered. FIG. 13H shows detection markers 1135. As shown, the detection markers 1135 may include round (or green) markers that indicate that measurements from two aperture verification systems match (e.g., causing a confidence of 80% or higher). The detection markers 1135 may additionally include square (or yellow) markers that indicate that measurements from the two aperture verification systems have a variation that exceeds a first threshold but that does not exceed a second threshold (e.g., causing a confidence of 60-80%). The detection markers 1135 may additionally include diamond (or red) markers that indicate that measurements from the two aperture verification systems have a variation that is greater than the second threshold (e.g., causing a confidence of less than 60%).

Figure 14A:
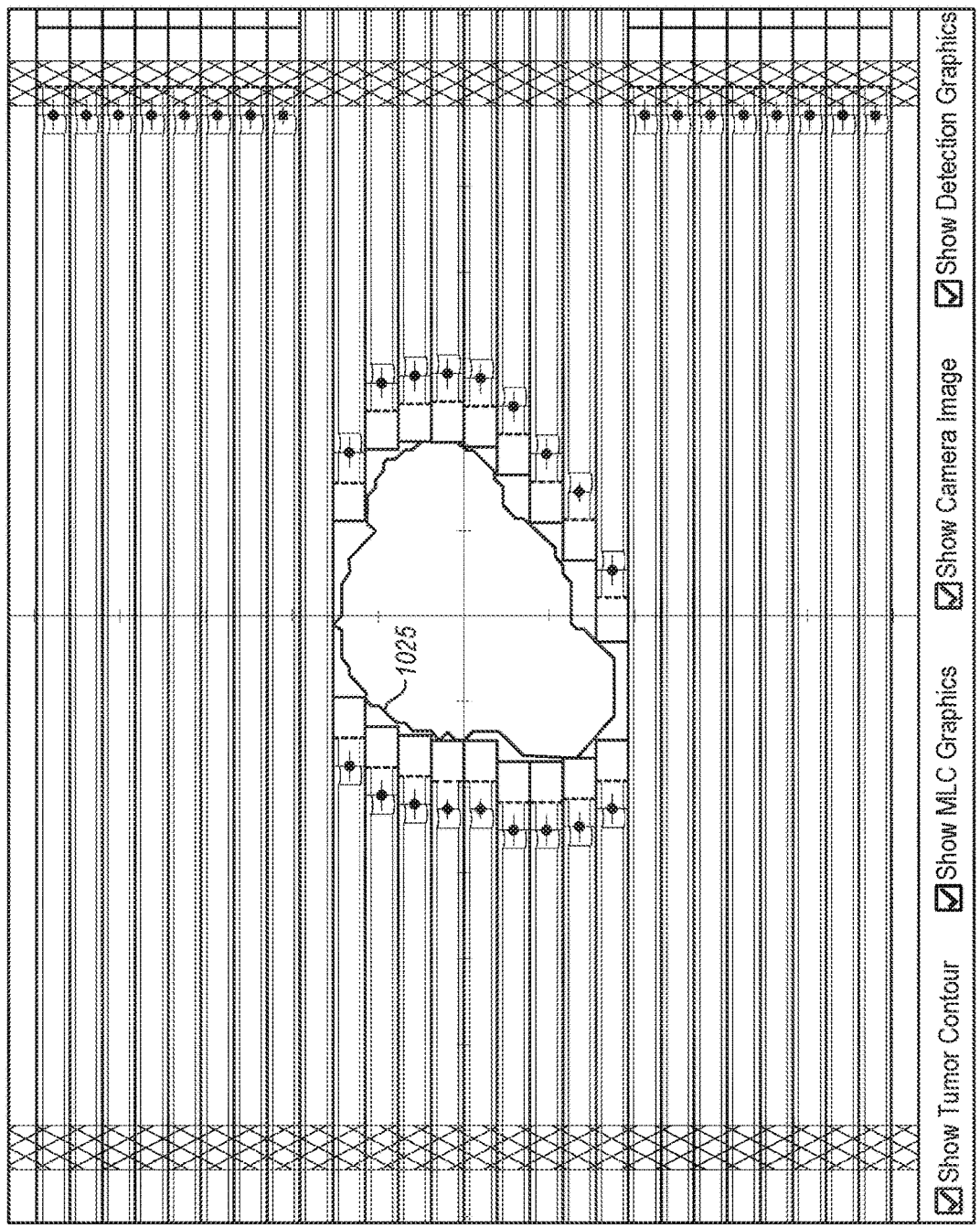
FIG. 14A illustrates a static image of an MLC aperture, in accordance with one embodiment.

FIGS. 14A-14D illustrate additional pictorial representations of an MLC aperture. FIG. 14A illustrates a diagram 1400 of a static image for an MLC aperture, similar to the diagram 1100 of FIG. 11. In diagram 1400, a show tumor contour check box, a show MLC graphics check box, a show camera image check box, and a show detection graphics check box are all checked. Accordingly, a non-distorted image of an MLC aperture is shown with overlays of detection graphics, MLC graphics and a tumor contour.

Figure 14B:
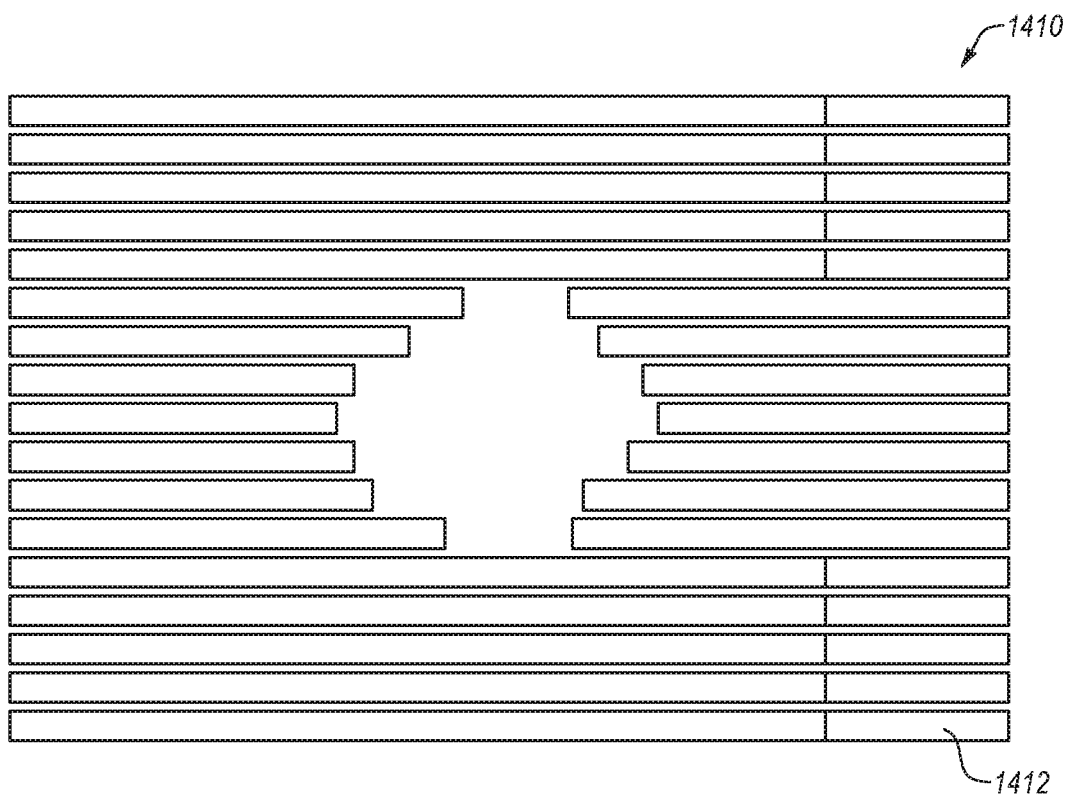
FIG. 14B illustrates a pictorial representation of an MLC aperture as determined by an aperture verification system other than an image-based aperture verification system, in accordance with one embodiment.
Figure 14C:
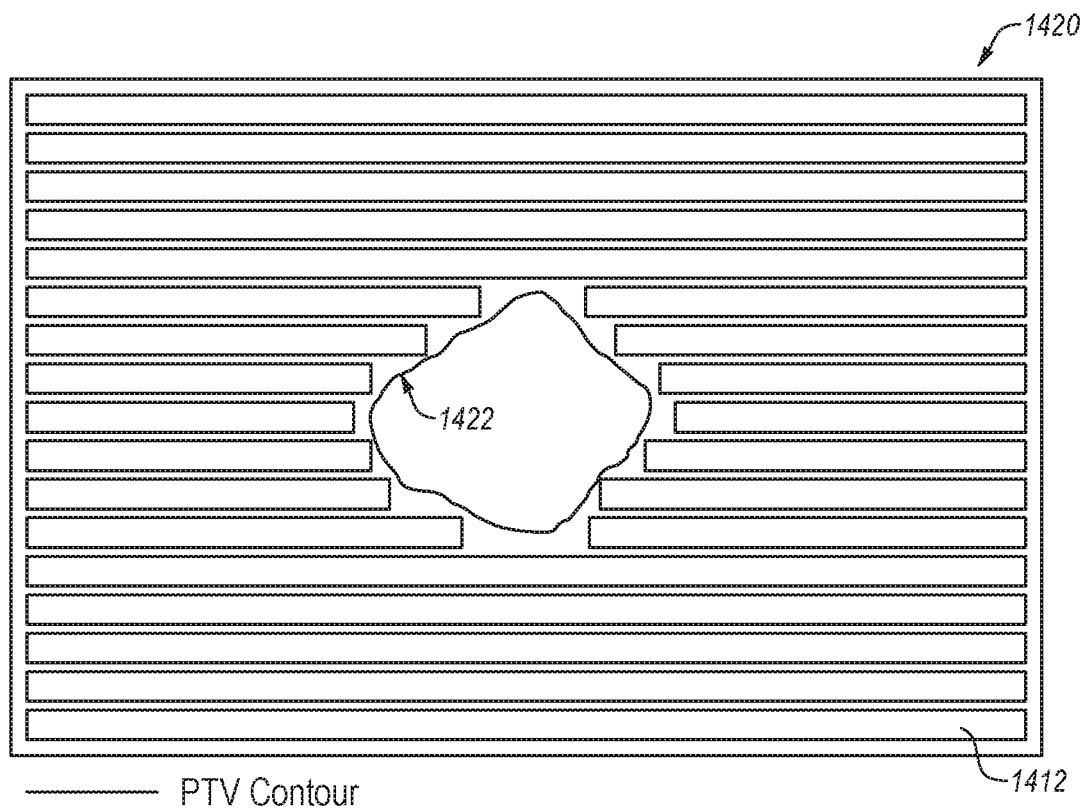
FIG. 14C illustrates positions of MLC leaves with an overlay of a tumor contour, in accordance with one embodiment.
Figure 14D:
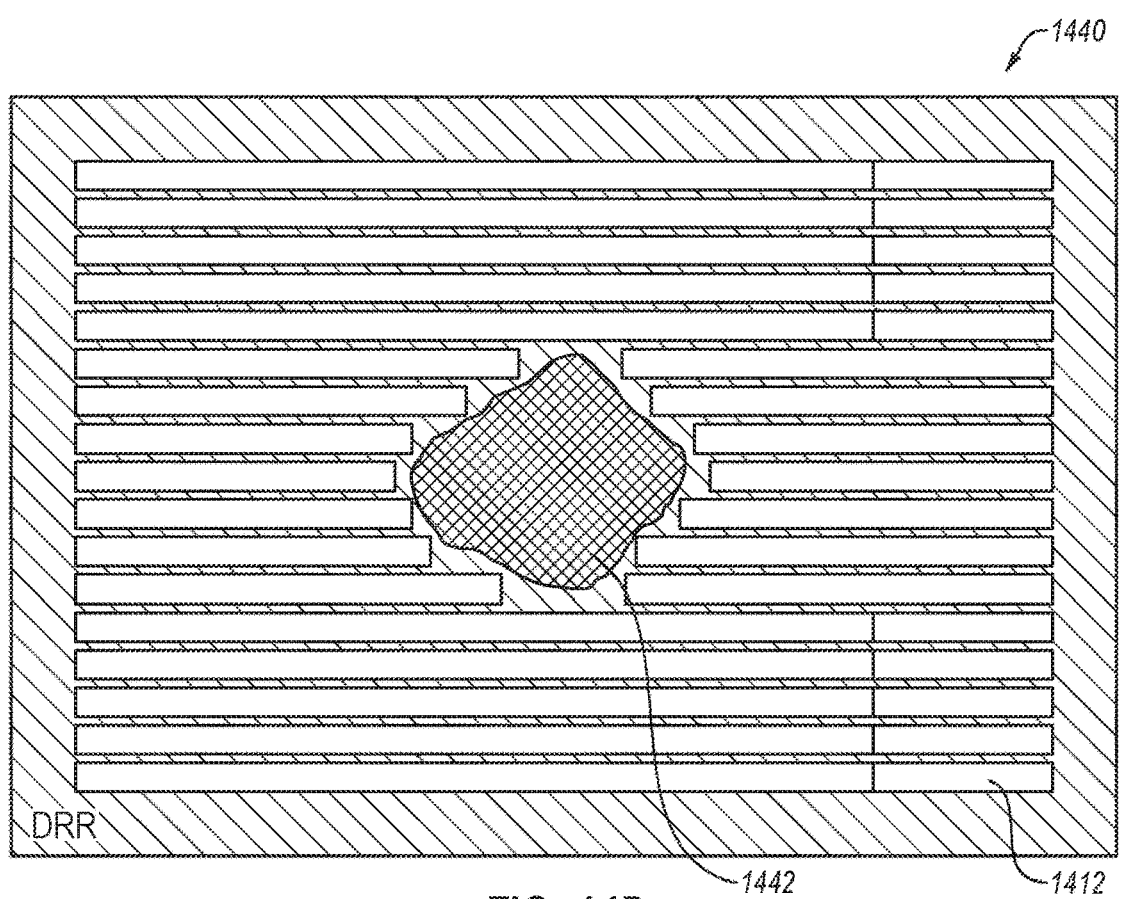
FIG. 14D illustrates a first diagram of positions of MLC leaves with an overlay of a computed DRR, in accordance with one embodiment.
Figure 14E:
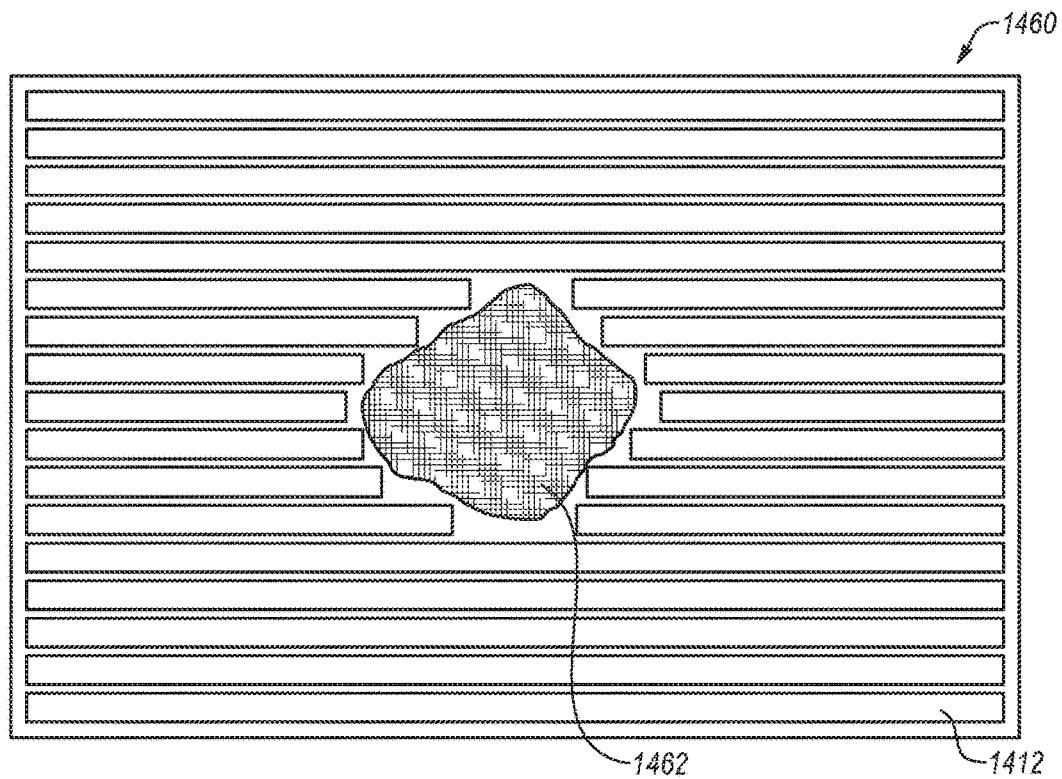
FIG. 14E illustrates a second diagram of positions of MLC leaves with an overlay of a computed DRR, in accordance with one embodiment.

FIG. 14B illustrates a diagram 1410 of just the computed positions of the MLC leaves 1412 as determined by an aperture verification system other than the image-based aperture verification system. FIG. 14C illustrates a diagram 1420 of the computed positions of the MLC leaves 1412 with an overlay of a tumor contour 1422. FIG. 14D illustrates a diagram 1440 of the computed positions of the MLC leaves 1412 with an overlay of a computed DRR 1442 generated from the perspective of the reference coordinate space. FIG. 14E illustrates another diagram 1460 of the computed positions of the MLC leaves 1412 with an overlay of a computed DRR 1462 generated from the perspective of the reference coordinate space.

Figure 14F:
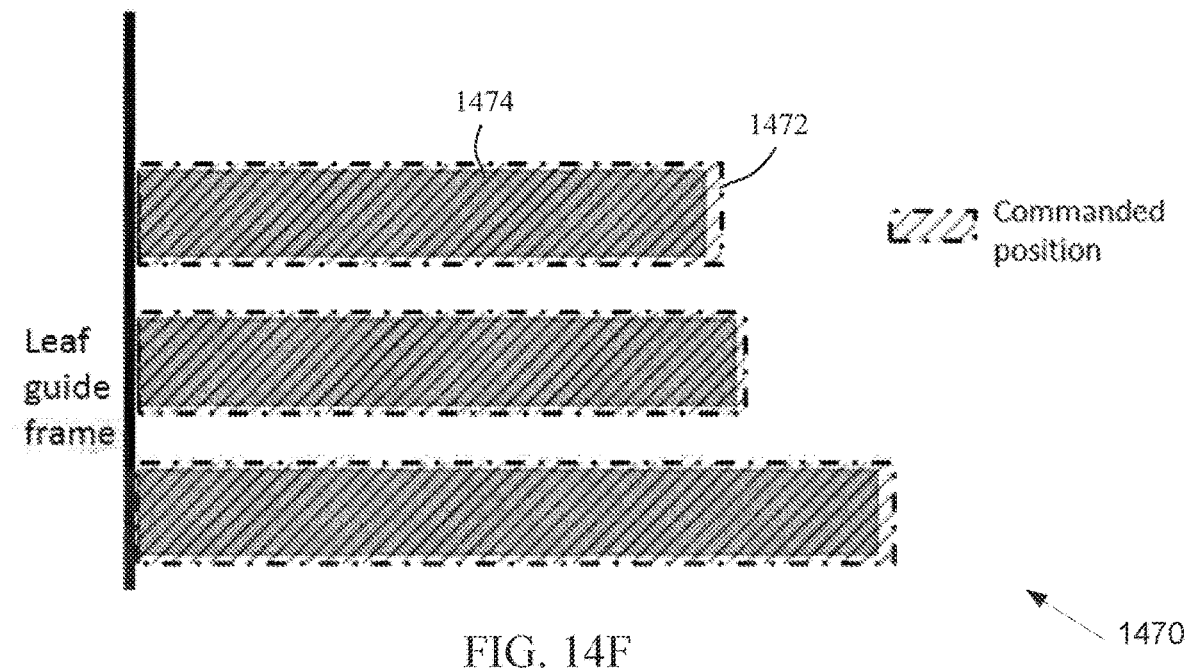
FIG. 14F illustrates a top-view image of leaves of an MLC with an overlay of MLC graphics, in accordance with one embodiment.
Figure 14G:
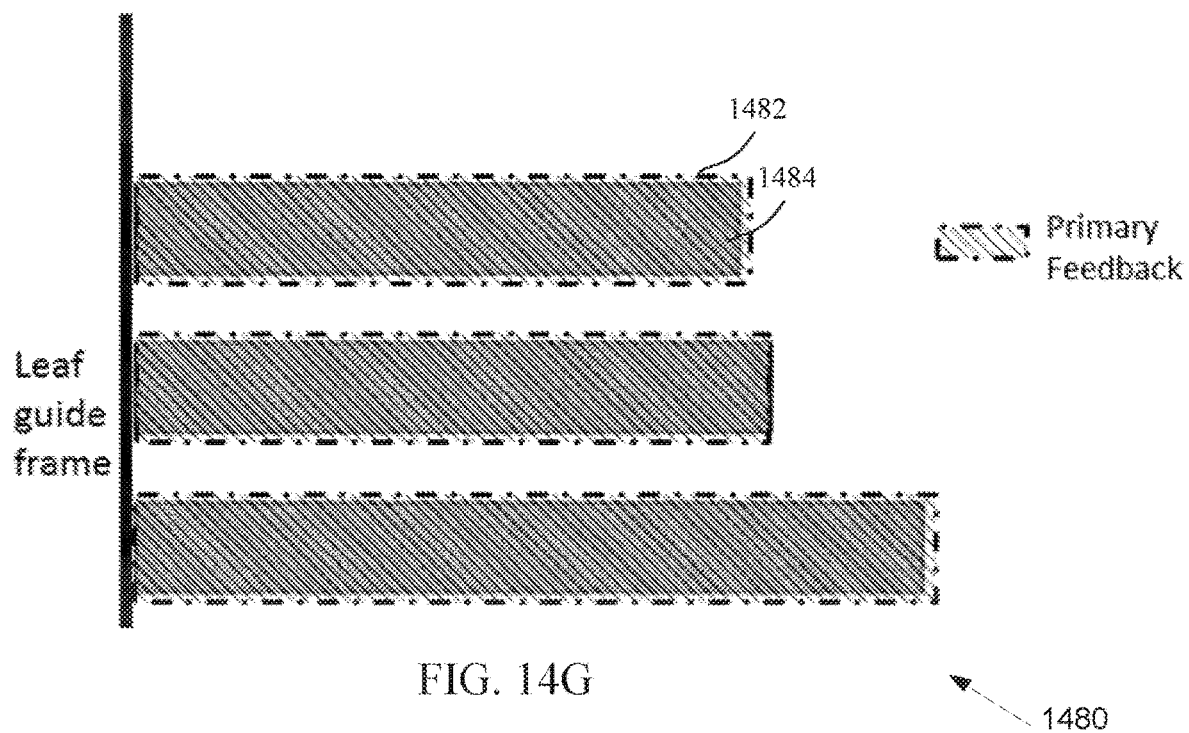
FIG. 14G illustrates a comparison between leaf positions as measured by an image-based aperture verification system and leaf positions as measured by an additional aperture verification system, in accordance with one embodiment.
Figure 14H:
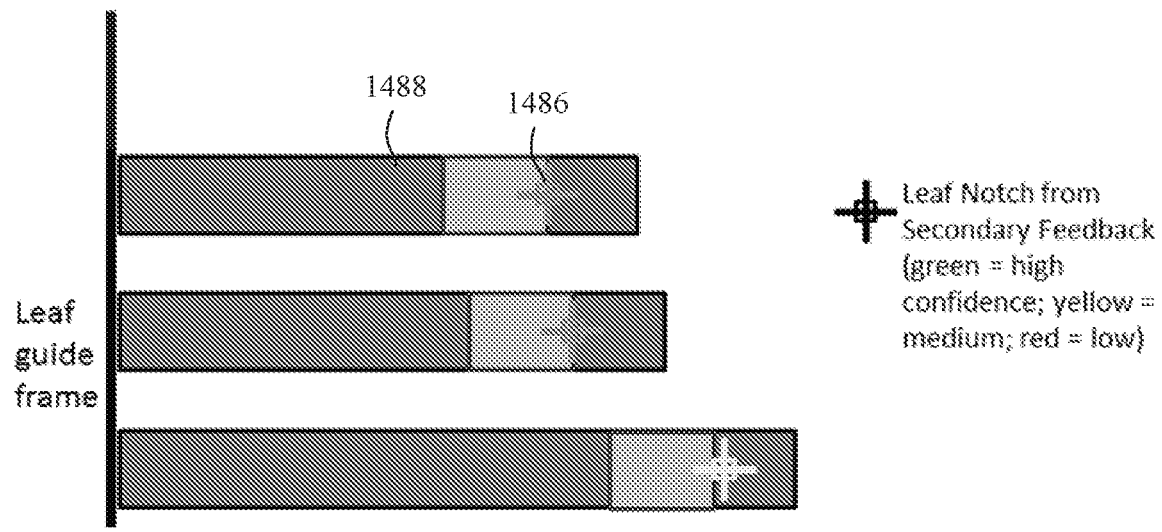
FIG. 14H illustrates an image of leaves of an MLC with an overlay of detection markers, in accordance with one embodiment.
Figure 14I:
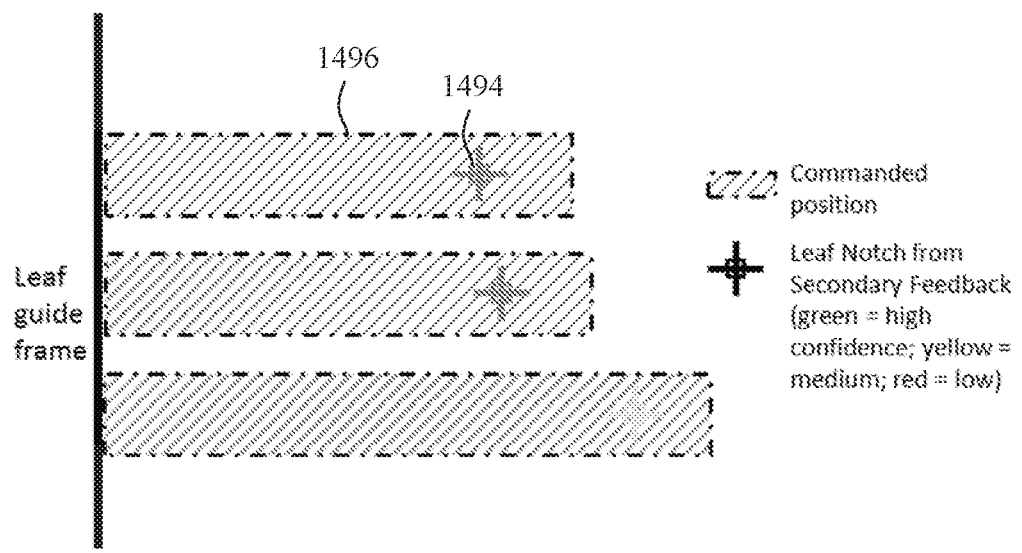
FIG. 14I illustrates detection markers of leaves for an MLC overlaid on a commanded position for those leaves, in accordance with one embodiment.

FIG. 14F illustrates a top-view image of leaves on an MLC (e.g., as generated by an image-based aperture verification system) with an overlay of MLC graphics. In particular, a comparison 1470 between a commanded position 1472 and an actual measured position 1474 are shown, where gray bars represent measured positions 1474 and a patterned region overlay represents a commanded position 1472. FIG. 14G shows a comparison 1480 between leaf positions 1482 as measured by a primary aperture verification system and leaf positions 1484 as measured by a secondary aperture verification system (e.g., an image-based aperture verification system). FIG. 14H illustrates detection markers 1486 on images of leaves 1488 as generated by an image sensor. FIG. 14I illustrates detection markers of leaves 1494 overlaid on a commanded position 1496.

Figure 15B:
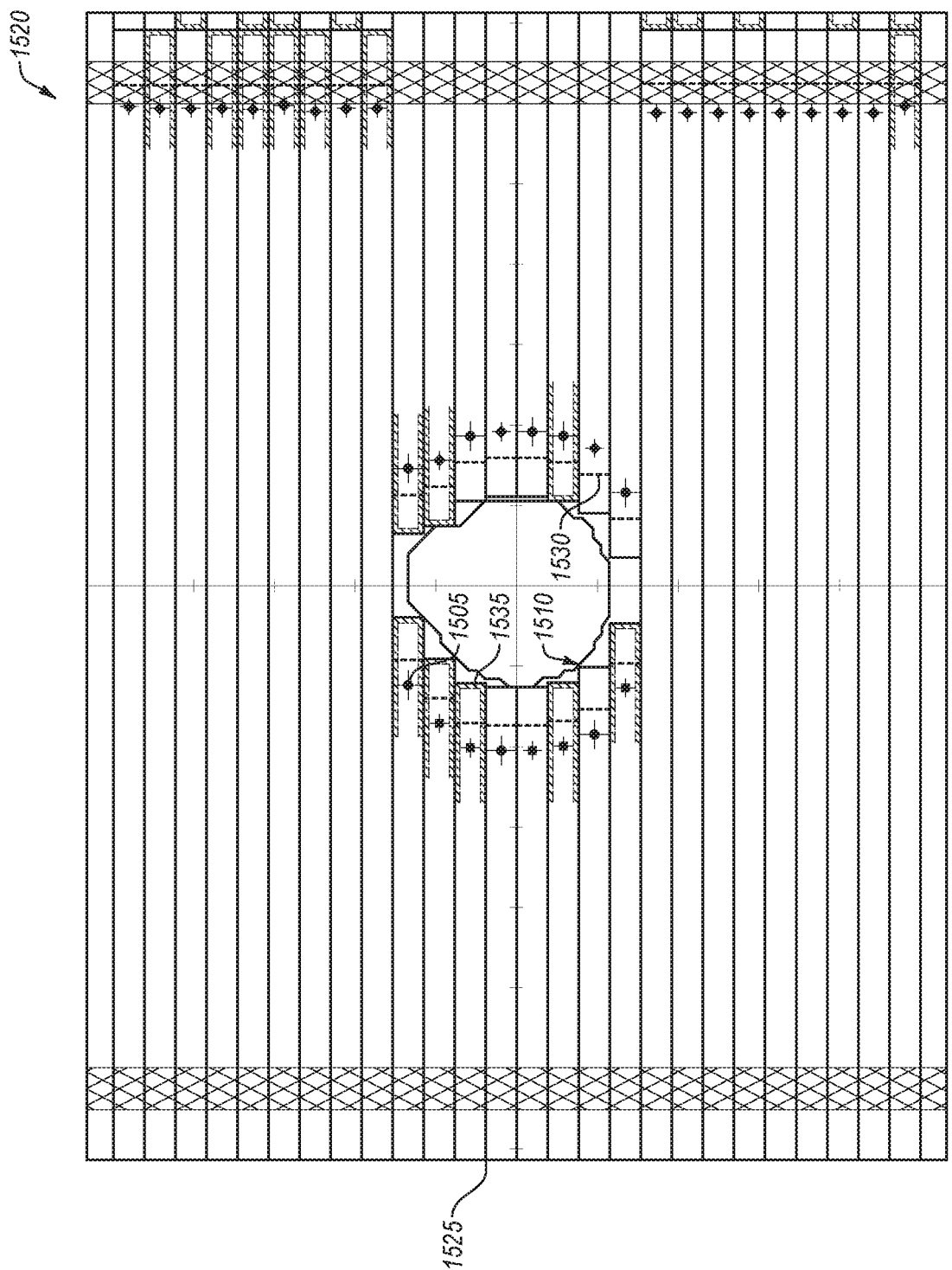
FIG. 15B illustrates the diagram of FIG. 15A additionally showing other MLC graphic overlays, in accordance with embodiments.
Figure 15C:
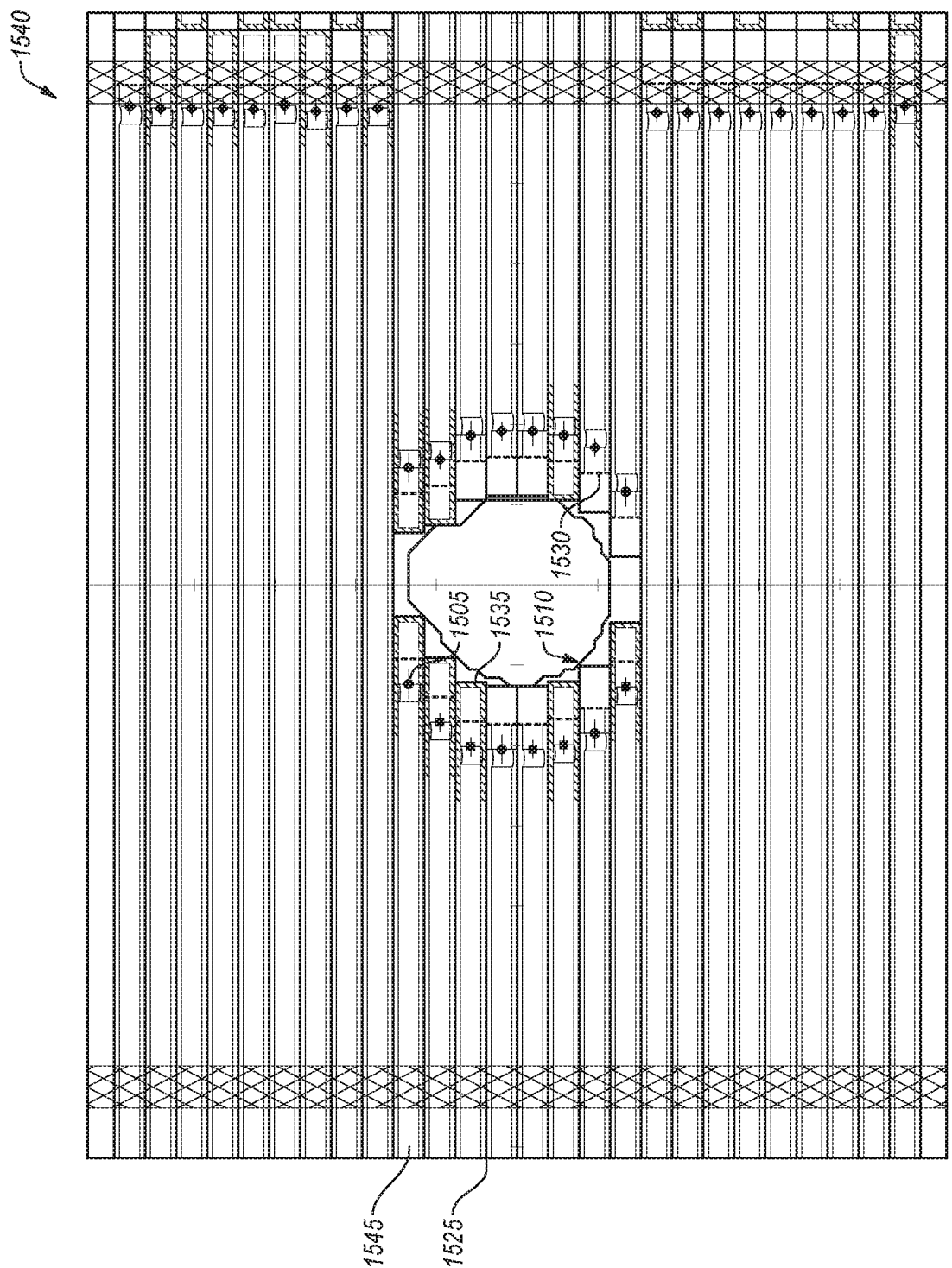
FIG. 15C illustrates the diagram of FIG. 15B additionally showing a top-view image of an MLC aperture as generated by an image-based aperture verification system, in accordance with embodiments.

FIGS. 15A-15C illustrate various views of an MLC aperture, in accordance with embodiments. FIG. 15A illustrates a diagram 1500 with detection markers 1505 and a tumor contour 1510 shown. In diagram 1500, a camera static image and MLC graphics have been disabled. FIG. 15B illustrates a diagram 1520 that corresponds to diagram 1500 after MLC graphics have been turned on. Diagram 1520 includes detection markers 1505 and tumor contour 1510, and additionally includes lines and rectangles 1525 showing leaf positions as measured by an aperture verification system, vertical lines 1530 that show visible edges of leaves and leaf alert borders 1535. FIG. 15C illustrates a diagram 1540 that corresponds to diagram 1520 after a camera static image has also been turned on. Accordingly, in diagram 1540 images of leaves 1545 from an image-based aperture verification system are shown.

Figure 15D:
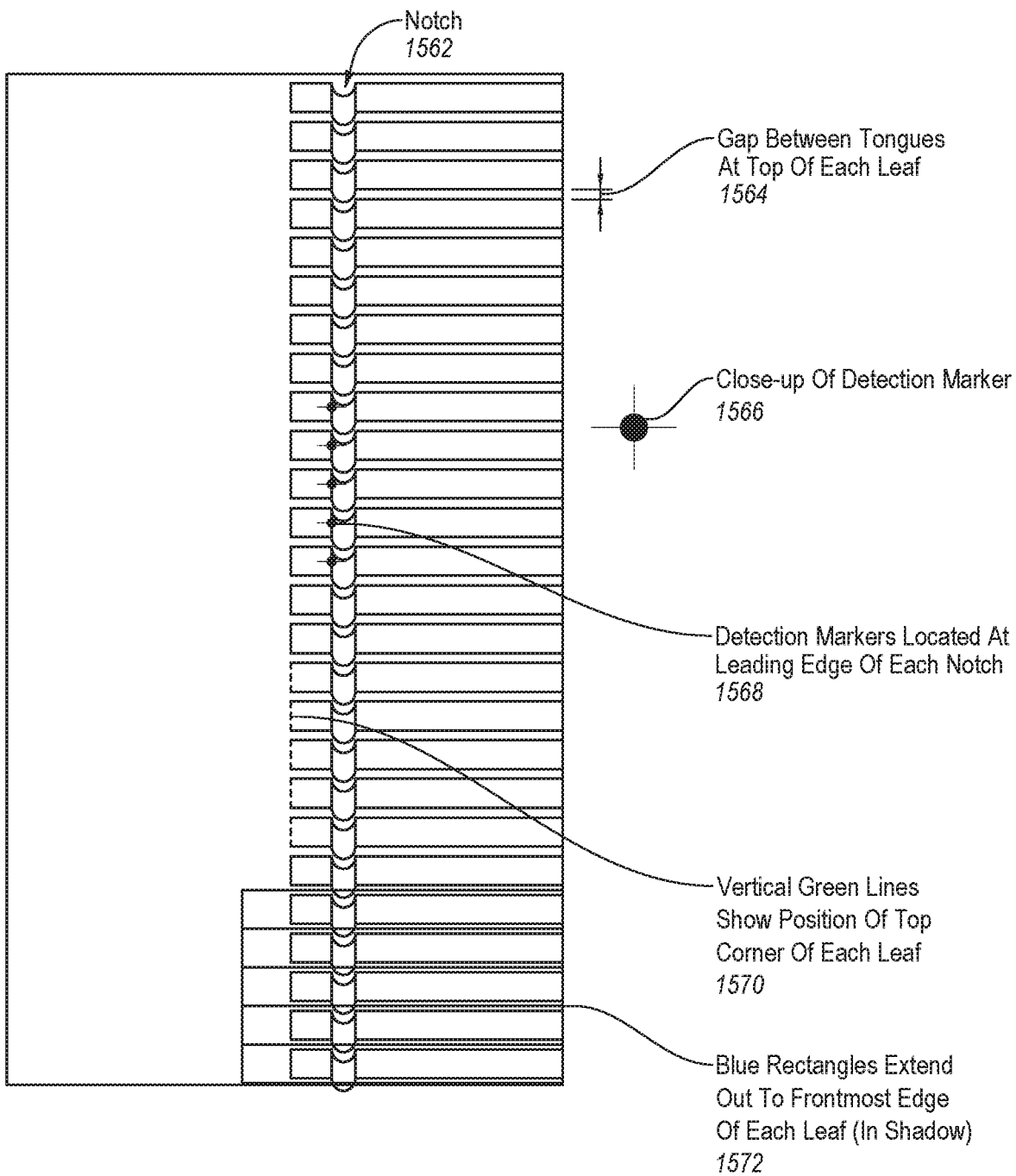
FIG. 15D illustrates an image of a portion of an MLC aperture with an overlay showing non-visible portions of leaves.

FIG. 15D illustrates an image of a portion of an MLC aperture with an overlay showing non-visible portions of leaves. In FIG. 15D, MLC graphics are overlaid on the leaves to provide additional information. The MLC graphics include rectangles 1572 that extend out to the front-most edge of each leaf, which is in shadow (e.g., see FIGS. 2-3). The MLC graphics additionally include vertical lines 1570 that show positions of the top corner of each leaf. The MLC graphics additionally include detection markers 1566 located at a leading edge of a notch 1562 in each leaf. FIG. 15D also shows a gap 1564 between the tongues at the top of each leaf.

Figure 16:
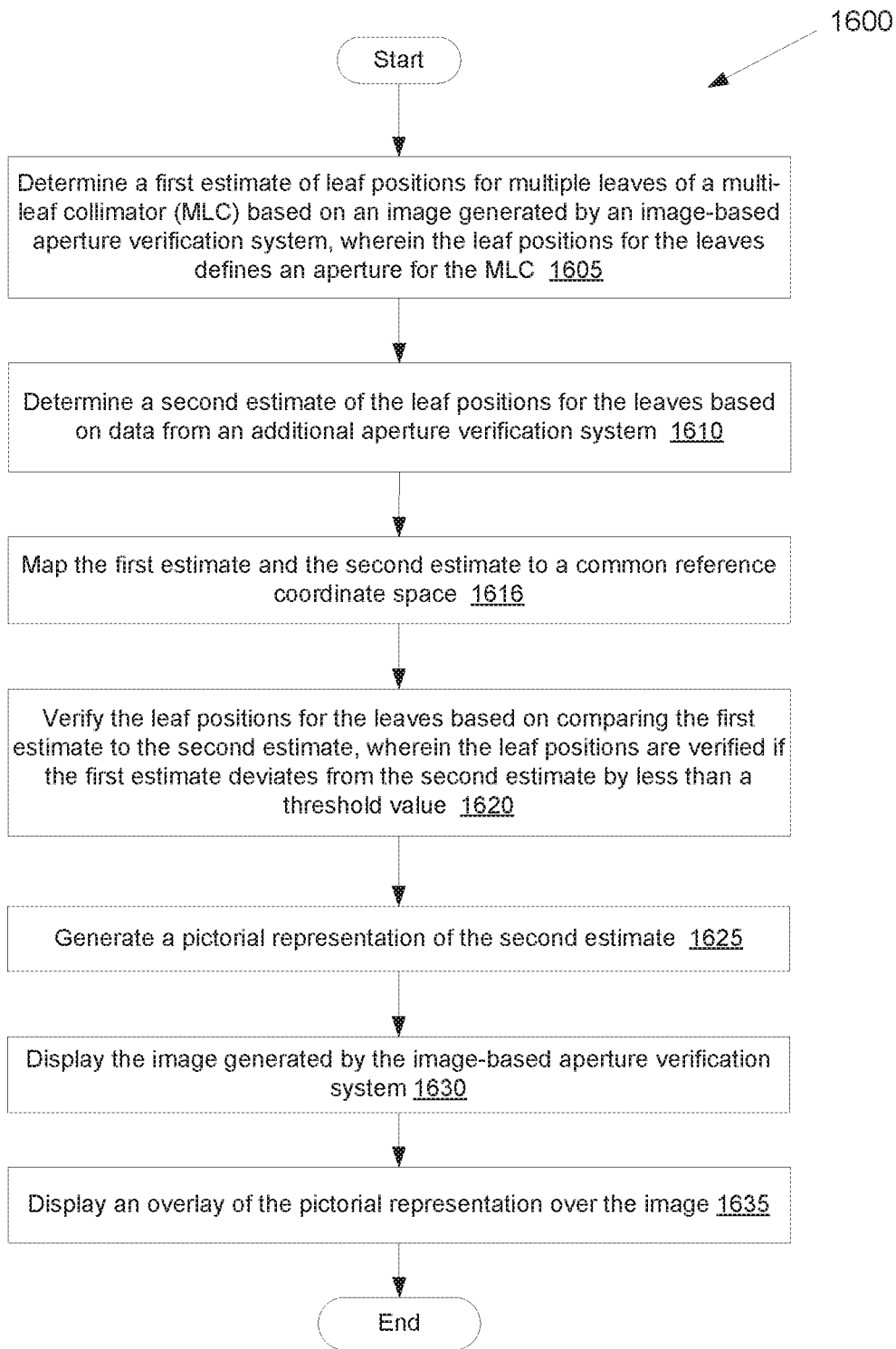
FIG. 16 illustrates one embodiment for a method of verifying an MLC aperture using an image-based aperture verification system and an additional aperture verification.

FIG. 16 illustrates one embodiment for a method 1600 of verifying an MLC aperture using an image-based aperture verification system and an additional aperture verification system. In other embodiments, the MLC aperture may be verified using an image-based aperture verification system and another data source, such as a treatment plan. Operations of method 1600 may be performed by an image-based aperture verification system, which may include an image sensor and a processing logic that processes data from the image sensor. Operations may also be performed by processing logic that controls an MLC and/or a radiation treatment device. The processing logic may include firmware, software, hardware, or a combination thereof. For example, the processing logic may include a processor executing one or more image processing algorithms.

At block 1605 of method 1600, processing logic determines a first estimate of leaf positions for multiple leaves of an MLC based on an image generated by an image-based aperture verification system, wherein the leaf positions for the leaves define an aperture for the MLC. The first estimate may be determined by transforming an oblique-view image of the leaves into a top-view image of the leaves as described above. The top-view image may have a reference coordinate space.

Once the oblique-view image is transformed into the top-view image having the reference coordinate space (also referred to as a reference coordinate system), the image can be broken into subdomains, where each subdomain corresponds to a single leaf. Image processing can then be performed within each subdomain to determine a leaf position of the leaf corresponding to that subdomain. In one embodiment, notches on the leaves are used as a proxy for leaf leading edge positions because the leading edge positions may not be visible. In other embodiments, one may use a proxy other than a notch. Any visual feature on the camera-facing side of the leaf can be used for tracking the leading edge of the leaf. Examples of other features that may be used as a proxy include colored beads affixed to the leaves, etched patterns in the leaves, etc.

In one embodiment, template matching is performed within each subdomain to look for the location with the highest normalized cross-correlation coefficient between an image block within the subdomain and a set of MLC leaf notch templates. Each MLC leaf notch template may be an image template of a particular leaf notch. The leaf notch may be used as a surrogate for the position of the leading edge of the leaf, because the actual tip of the leaf (as shown in FIGS. 2-3) is not visible on the camera. Leaf edges are detected with one or more leaf edge templates, which are defined as sub-images representing the appearance of the tip of a leaf as seen from a camera. A leaf edge template has a vertical size approximately twice the width of a leaf and a horizontal size approximately four times the vertical size. The leaf edge templates in this case include the tip of the leaf and some space extending beyond the tip, the notch on the leaf, and a portion of the leaf extending beyond the notch toward the guide frame. The position of the side of the notch closest to the leaf tip is known in each leaf edge template. Accordingly, when a matching region in the image is determined the location of the edge of the leaf, which is not visible on the image sensor, is also known via the mechanical design of the leaf as shown in FIGS. 2-3. When the notch is detected, the delta or offset between the notch and the end of the leaf may be factored in to accurately determine a position of the end of the leaf.

At block 1610, processing logic determines a second estimate of leaf positions for the leaves based on data from an additional aperture verification system. The second estimate may be determined for each leaf based on a reading from a displacement gauge or encoder for that leaf. Each displacement gauge or encoder value may correspond to a particular leaf position. Alternatively, or additionally, at block 1610 processing logic may determine planned leaf positions of a treatment plan.

At block 1616, processing logic may map the first estimate and the second estimate (and/or values of the planned leaf positions from the treatment plan) to a common reference coordinate space (RCS). In one embodiment, transforming of the oblique-view image to the top view image automatically maps the first estimate to the RCS. In one embodiment, determining the leaf positions corresponding to the encoder values for each leaf automatically maps the second estimate to the RCS.

At block 1620, processing logic verifies the leaf positions for the leaves based on comparing the first estimate to the second estimate (and/or to second values of the planned leaf positions from the treatment plan), wherein the leaf positions are verified if the first estimate deviates from the second estimate by less than a threshold value. In one embodiment, multiple threshold values are applied. In one embodiment, a confidence value is determined for each leaf position based on a comparison of the first and second estimates. In a further embodiment, a first confidence threshold of 60% and a second confidence threshold of 80% are applied. If a position for a leaf has a confidence value of less than 60%, then the system may generate an error, and treatment may halt. If a position for a leaf is between 60% and 80%, then the system may issue a warning, but treatment may continue. If a position for a leaf has a confidence of 80% or greater, then the system may determine that the position of the leaf is precisely known. Processing logic may also verify the leaf positions by comparing the first estimate and/or the second estimate to a prescribed aperture defined in a treatment plan, which may also be mapped to the reference coordinate space.

At block 1625, processing logic generates a pictorial representation of the second estimate. At block 1630, processing logic displays the image generated by the image-based aperture verification system. At block 1635, processing logic displays an overlay of the pictorial representation over the image. Processing logic may also generate graphics based on the first estimate from the image-based aperture verification system, and may overlay these graphics on the image. The graphics may include lines showing the top visible edges of leaves, detection markers (which may be lined up with notches in the leaves), shading representing leaf movement, leaf alert borders, lines representing the leading edges of leaves, and so on. Additionally, processing logic may generate a pictorial representation of a tumor and/or a DRR, and overlay one of both of these on the image. Other pictorial representations/graphics may be generated and displayed in conjunction with the image as well.

In a video mode, new data is continually processed and updates to the image and the overlays are continually made. Thus, a user may witness leaf positions and additional data in real time or near real time. For example, a new image may be generated 4 times per second, 10 times per second, 5 times per second, 2 times per second, 1 time per two seconds, and so on.

Figure 17:
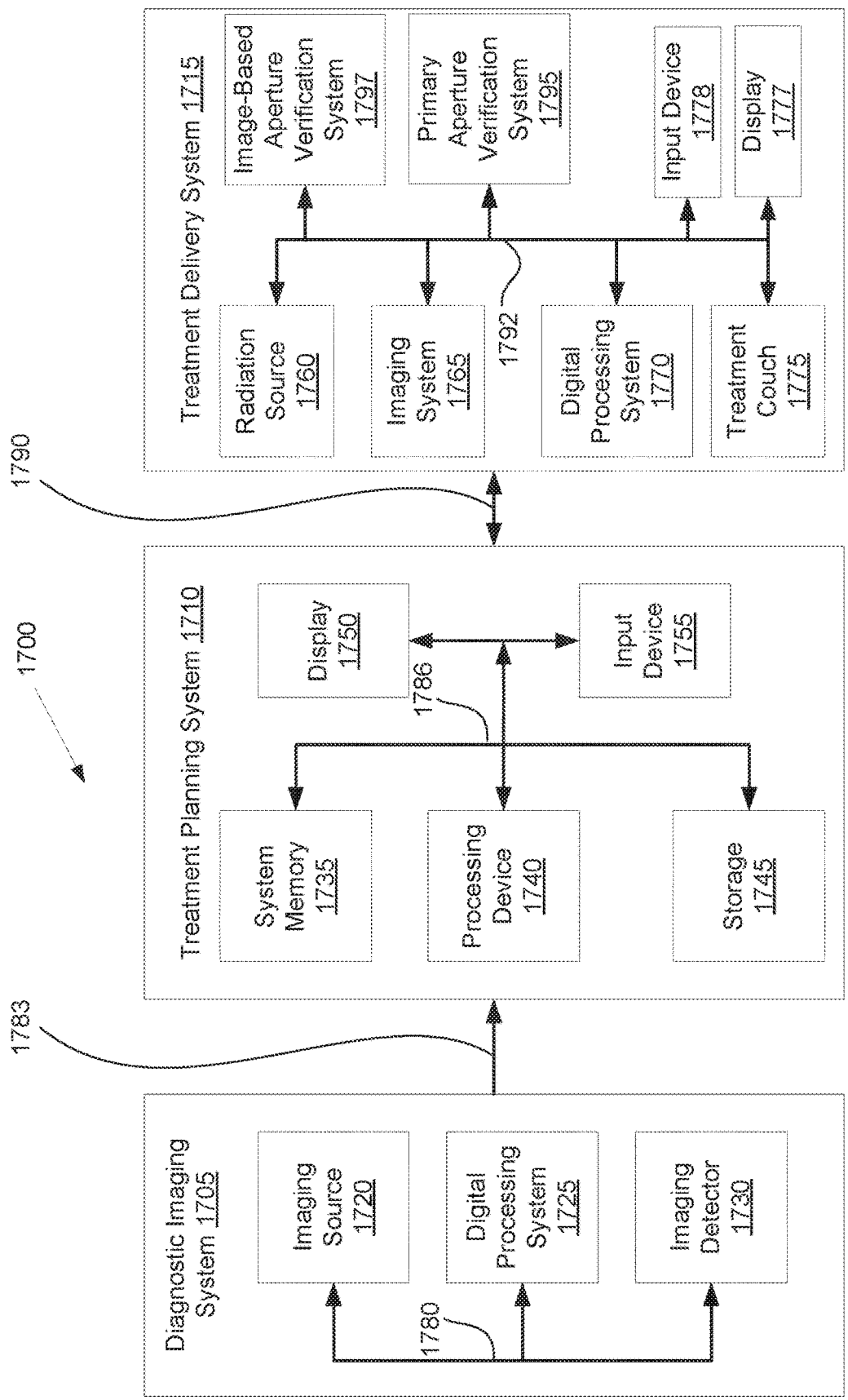
FIG. 17 illustrates one embodiment of systems that may be used in performing radiation treatment.

FIG. 17 illustrates one embodiment of systems that may be used in generating a treatment plan and/or performing radiation treatment. These systems may be used to perform, for example, the methods described above. As described below and illustrated in FIG. 17, a system 1700 may include a diagnostic imaging system 1705, a treatment planning system 1710, a treatment delivery system 1715 and a motion detecting system (not shown). In one embodiment, the diagnostic imaging system 1705 and the motion detecting system are combined into a single unit.

Diagnostic imaging system 1705 may be any system capable of producing medical diagnostic images of a patient that may be used for subsequent medical diagnosis, treatment planning, treatment simulation and/or treatment delivery. For example, diagnostic imaging system 1705 may be a computed tomography (CT) system, a magnetic resonance imaging (MRI) system, a positron emission tomography (PET) system, or the like. For ease of discussion, diagnostic imaging system 1705 may be discussed below at times in relation to an x-ray imaging modality. However, other imaging modalities such as those above may also be used.

In one embodiment, diagnostic imaging system 1705 includes an imaging source 1720 to generate an imaging beam (e.g., x-rays) and an imaging detector 1730 to detect and receive the imaging beam generated by imaging source 1720, or a secondary beam or emission stimulated by the beam from the imaging source (e.g., in an MRI or PET scan).

The imaging source 1720 and the imaging detector 1730 may be coupled to a digital processing system 1725 to control the imaging operation and process image data. In one embodiment, diagnostic imaging system 1705 may receive imaging commands from treatment delivery system 1715.

Diagnostic imaging system 1705 includes a bus or other means 1780 for transferring data and commands among digital processing system 1725, imaging source 1720 and imaging detector 1730. Digital processing system 1725 may include one or more general-purpose processors (e.g., a microprocessor), special purpose processor such as a digital signal processor (DSP) or other type of device such as a controller or field programmable gate array (FPGA). Digital processing system 1725 may also include other components (not shown) such as memory, storage devices, network adapters and the like. Digital processing system 1725 may be configured to generate digital diagnostic images in a standard format, such as the DICOM (Digital Imaging and Communications in Medicine) format, for example. In other embodiments, digital processing system 1725 may generate other standard or non-standard digital image formats. Digital processing system 1725 may transmit diagnostic image files (e.g., the aforementioned DICOM formatted files) to treatment delivery system 1715 over a data link 1783, which may be, for example, a direct link, a local area network (LAN) link or a wide area network (WAN) link such as the Internet. In addition, the information transferred between systems may either be pulled or pushed across the communication medium connecting the systems, such as in a remote diagnosis or treatment planning configuration. In remote diagnosis or treatment planning, a user may utilize embodiments of the present invention to diagnose or treat a patient despite the existence of a physical separation between the system user and the patient.

Treatment delivery system 1715 includes a therapeutic and/or surgical radiation source 1760 to administer a prescribed radiation dose to a target volume in conformance with a treatment plan. The radiation source 1760 may be connected to an MLC described in embodiments herein. Treatment delivery system 1715 may also include a digital processing system 1770 to control radiation source 1760, image-based aperture verification system 1797, primary aperture verification system 1795 and/or MLC, receive and process data from an imaging system 1765, and control a patient support device such as a treatment couch 1775. Alternatively or additionally, image-based aperture verification system 1797 may include its own processing device, which may perform operations described herein. Digital processing system 1770 may be configured to register 2D radiographic images received from diagnostic imaging system 1705, from two or more stereoscopic projections, with digitally reconstructed radiographs (DRRs) generated by digital processing system 1725 in diagnostic imaging system 1705 and/or DRRs generated by processing device 1740 in treatment planning system 1710. Digital processing system 1770 may include one or more general-purpose processors (e.g., a microprocessor), special purpose processor such as a digital signal processor (DSP) or other type of device such as a controller or field programmable gate array (FPGA). Similarly, a processing device of image-based aperture verification system 1797 may include one or more general-purpose processors (e.g., a microprocessor), special purpose processor such as a digital signal processor (DSP) or other type of device such as a controller or field programmable gate array (FPGA). Digital processing system 1770 and/or image based aperture verification system 1797 may also include other components (not shown) such as memory, storage devices, network adapters and the like.

In one embodiment, digital processing system 1770 includes system memory that may include a random access memory (RAM), or other dynamic storage devices, coupled to a processing device, for storing information and instructions to be executed by the processing device. The system memory also may be used for storing temporary variables or other intermediate information during execution of instructions by the processing device. The system memory may also include a read only memory (ROM) and/or other static storage device for storing static information and instructions for the processing device.

Digital processing system 1770 may also include a storage device, representing one or more storage devices (e.g., a magnetic disk drive or optical disk drive) for storing information and instructions. The storage device may be used for storing instructions for performing the treatment delivery steps discussed herein. Digital processing system 1770 may be coupled to radiation source 1760 and treatment couch 1775 (and an MLC) by a bus 1792 or other type of control and communication interface.

Digital processing system 1770 may implement methods to manage timing of diagnostic x-ray imaging in order to maintain alignment of a target with a radiation treatment beam delivered by the radiation source 1760. Digital processing system 1770 may additional implement methods to control the aperture of an MLC.

In one embodiment, the treatment delivery system 1715 includes an input device 1778 and a display 1777 connected with digital processing system 1770 via bus 1792. The display 1777 can show an aperture of the MLC, including a top-view image of the MLC aperture generated by an image-based aperture verification system, a pictorial representation of the MLC aperture as measured by an additional aperture verification system and/or additional overlays discussed above. The display 1777 can also show trend data that identifies a rate of target movement (e.g., a rate of movement of a target volume that is under treatment). The display can also show a current radiation exposure of a patient and a projected radiation exposure for the patient. The input device 1778 can enable a clinician to adjust parameters of a treatment delivery plan during treatment.

Treatment planning system 1710 includes a processing device 1740 to generate and modify treatment plans and/or simulation plans. Processing device 1740 may represent one or more general-purpose processors (e.g., a microprocessor), special purpose processor such as a digital signal processor (DSP) or other type of device such as a controller or field programmable gate array (FPGA). Processing device 1740 may be configured to execute instructions for performing treatment planning operations.

Treatment planning system 1710 may also include system memory 1735 that may include a random access memory (RAM), or other dynamic storage devices, coupled to processing device 1740 by bus 1786, for storing information and instructions to be executed by processing device 1740. System memory 1735 also may be used for storing temporary variables or other intermediate information during execution of instructions by processing device 1740. System memory 1735 may also include a read only memory (ROM) and/or other static storage device coupled to bus 1786 for storing static information and instructions for processing device 1740.

Treatment planning system 1710 may also include storage 1745, representing one or more storage devices (e.g., a magnetic disk drive or optical disk drive) coupled to bus 1786 for storing information and instructions. Storage 1745 may be used for storing instructions for performing treatment planning.

Processing device 1740 may also be coupled to a display device 1750, such as a cathode ray tube (CRT) or liquid crystal display (LCD), for displaying information (e.g., a 2D or 3D representation of a volume of interest (VOI)) to a user. An input device 1755, such as a keyboard, may be coupled to processing device 1740 for communicating information and/or command selections to processing device 1740. One or more other user input devices (e.g., a mouse, a trackball or cursor direction keys) may also be used to communicate directional information, to select commands for processing device 1740 and to control cursor movements on display 1750.

Treatment planning system 1710 may share its database (e.g., data stored in storage 1745) with a treatment delivery system, such as treatment delivery system 1715, so that it may not be necessary to export from the treatment planning system prior to treatment delivery. Treatment planning system 1710 may be linked to treatment delivery system 1715 via a data link 1790, which may be a direct link, a LAN link or a WAN link.

It should be noted that when data links 1783 and 1790 are implemented as LAN or WAN connections, any of diagnostic imaging system 1705, treatment planning system 1710 and/or treatment delivery system 1715 may be in decentralized locations such that the systems may be physically remote from each other. Alternatively, any of diagnostic imaging system 1705, treatment planning system 1710, and/or treatment delivery system 1715 may be integrated with each other in one or more systems.

Figure 18:
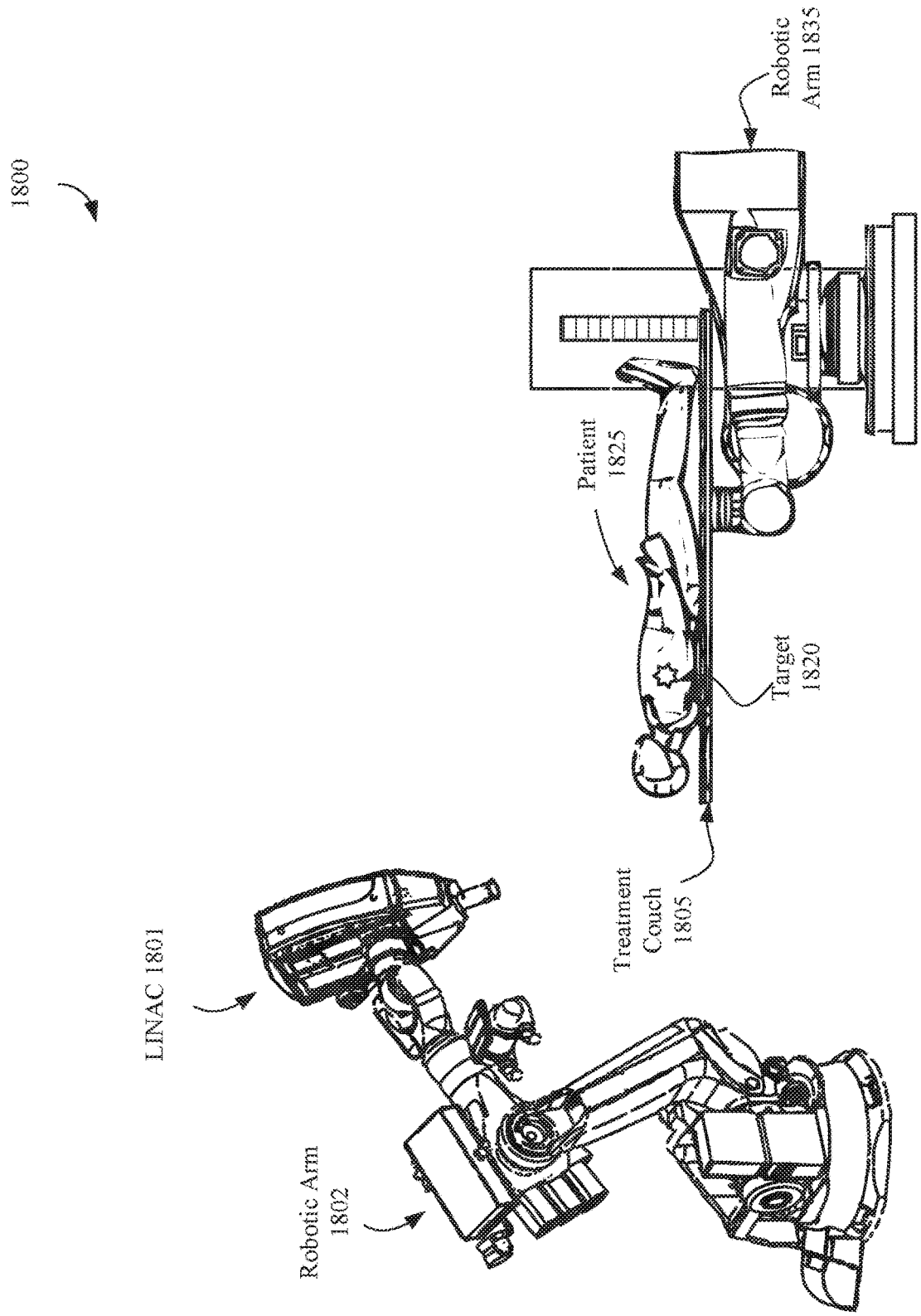
FIG. 18 illustrates a configuration of an image-guided radiation treatment system, in accordance with embodiments of the present invention.

FIG. 18 illustrates a configuration of an image-guided radiation treatment system 1800, in accordance with embodiments of the present invention. In the illustrated embodiment, the radiation treatment system 1800 includes a linear accelerator (LINAC) 1801 that acts as a radiation treatment source. The LINAC 1801 is mounted on the end of a robotic arm 1802 having multiple (e.g., 5 or more) degrees of freedom in order to position the LINAC 1801 to irradiate a pathological anatomy (e.g., target 1820) with beams delivered from many angles, in many planes, in an operating volume around a patient. Treatment may involve beam paths with a single isocenter, multiple isocenters, or with a non-isocentric approach. Alternatively, other types of image guided radiation treatment (IGRT) systems may be used. In one alternative embodiment, the LINAC 1801 may be mounted on a gantry based system to provide isocentric beam paths. In one particular embodiment, the IGRT system is the Vero SBRT System (referred to as TM200 in Japan), a joint product of Mitsubishi Heavy Industries Ltd., of Tokyo Japan and BrainLAB AG of Germany, that utilizes a rigid O-ring based gantry. Such an O-ring based gantry system is described in greater detail below with reference to FIG. 19.

The LINAC 1801 may be positioned at multiple different nodes (predefined positions at which the robot stops and radiation may be delivered) during treatment by moving the robotic arm 1802. At the nodes, the LINAC 1801 can deliver one or more radiation treatment beams to a target. The nodes may be arranged in an approximately spherical distribution about a patient. The particular number of nodes and the number of treatment beams applied at each node may vary as a function of the location and type of pathological anatomy to be treated. For example, the number of nodes may vary from 50 to 300, or more preferably 15 to 100 nodes and the number of beams may vary from 1200 to 3200, or more preferably 50 to 300. LINAC 1801 may include a multi-leaf collimator (not shown) as described in embodiments herein mounted to a front of the LINAC 1801 along a beam path.

The LINAC 1801 may be connected to a radiation treatment system (not shown) which may include an imaging system having a processor connected with x-ray sources and x-ray detectors. The imaging system may perform computed tomography (CT) such as cone beam CT, and images generated by the imaging system may be two-dimensional (2D) or three-dimensional (3D). The imaging system may be used to provide a reference point for positioning a patient 1825 on a treatment couch 1805 during treatment. A robotic arm 1835 may position a treatment couch 1805 that supports the patient 1825 during treatment.

Figure 19:
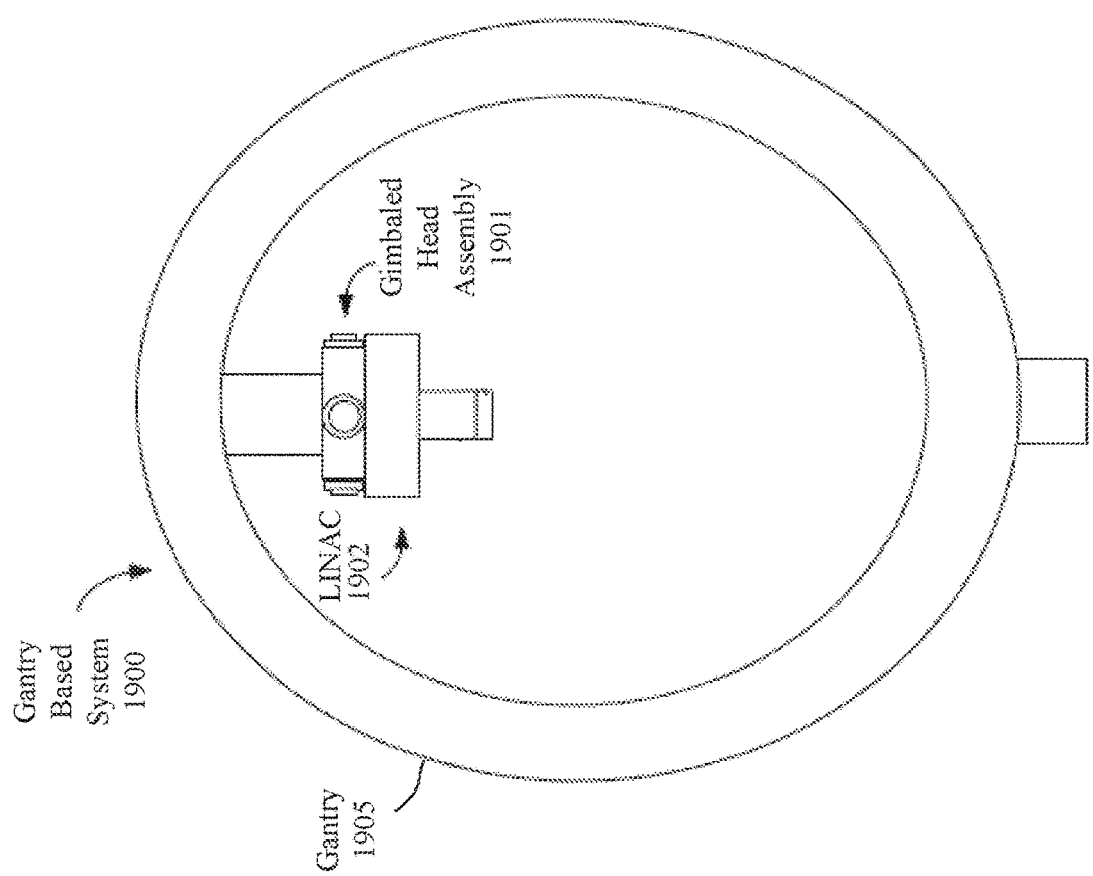
FIG. 19 illustrates a gantry based image-guided radiation treatment system, in accordance with embodiments of the present invention.

FIG. 19 illustrates one embodiment of a gantry based (isocentric) intensity modulated radiotherapy (IMRT) system 1900. In a gantry based IMRT system 1900, a radiation source (e.g., a LINAC) 1902 is mounted on a gantry 1905 in such a way that it rotates in a plane corresponding to an axial slice of the patient. Radiation is then delivered from several positions on the circular plane of rotation. In IMRT, the shape of the radiation beam is defined by a multi-leaf collimator (MLC) that allows portions of the beam to be blocked, so that the remaining beam incident on the patient has a pre-defined shape. The resulting system generates arbitrarily shaped radiation beams that intersect each other at the isocenter to deliver a dose distribution to the target. The MLC mounted to the LINAC 1902 is an MLC described in embodiments herein.

In one embodiment, the gantry based IMRT system 1900 is an o-ring based system having a gimbaled radiation source head assembly 1901. The o-ring can be skewed around its vertical axis, and one or more gimbals can be driven to rotate in pan and tilt directions in order to position the LINAC 1902. In one embodiment, the gantry 1905 rotates 360 degrees about a horizontal axis, and additionally allows rotation about a vertical axis (a so called skew) of +/−60 degrees. Orthogonal gimbals hold the LINAC 1902, which allows pan and tilt motions of the LINAC. This system may include dual orthogonal imaging systems at 45 degrees from the treatment beam, to allow for the acquisition of x-ray images. In another embodiment, the gantry based IMRT system 1900 is a c-arm based system, as manufactured by Varian®.

It will be apparent from the foregoing description that aspects of the present invention may be embodied, at least in part, in software. That is, the techniques may be carried out in a computer system or other data processing system in response to its processor, such as digital processing system 1770, for example, executing sequences of instructions contained in a memory. In various embodiments, hardware circuitry may be used in combination with software instructions to implement embodiments of the present invention. Thus, the techniques are not limited to any specific combination of hardware circuitry and software or to any particular source for the instructions executed by the digital processing system 1770. In addition, throughout this description, various functions and operations may be described as being performed by or caused by software code to simplify description. However, those skilled in the art will recognize what is meant by such expressions is that the functions result from execution of the code by a processor or controller, such as digital processing system 1770.

A computer-readable medium can be used to store software and data which when executed by a general purpose or special purpose processing device causes the processing device to perform various methods of the present invention. This executable software and data may be stored in various places including, for example, system memory and storage or any other device that is capable of storing software programs and/or data. Thus, a computer-readable medium includes any mechanism that provides (i.e., stores) information in a form accessible by a machine (e.g., a computer, network device, personal digital assistant, manufacturing tool, any device with a set of one or more processors, etc.). For example, a computer-readable medium includes recordable/non-recordable media such as read only memory (ROM), random access memory (RAM), magnetic disk storage media, optical storage media, flash memory devices, etc.

Unless stated otherwise as apparent from the foregoing discussion, it will be appreciated that terms such as "processing," "computing," "generating," "comparing" "determining," "verifying," "mapping," "transforming," or the like may refer to the actions and processes of a computer system, or similar electronic computing device, that manipulates and transforms data represented as physical (e.g., electronic) quantities within the computer system's registers and memories into other data similarly represented as physical quantities within the computer system's memories or registers or other such information storage or display devices. Embodiments of the methods described herein may be implemented using computer software. If written in a programming language conforming to a recognized standard, sequences of instructions designed to implement the methods can be compiled for execution on a variety of hardware platforms and for interface to a variety of operating systems. In addition, embodiments of the present invention are not described with reference to any particular programming language. It will be appreciated that a variety of programming languages may be used to implement embodiments of the present invention.

It should be noted that the methods and apparatus described herein are not limited to use only with medical diagnostic imaging and treatment. In alternative embodiments, the methods and apparatus herein may be used in applications outside of the medical technology field, such as industrial imaging and non-destructive testing of materials. In such applications, for example, "treatment" may refer generally to the effectuation of an operation controlled by the treatment planning system, such as the application of a beam (e.g., radiation, acoustic, etc.) and "target" may refer to a non-anatomical object or area.

In the foregoing specification, embodiments of the invention have been described with reference to specific examples. It will, however, be evident that various modifications and changes may be made thereto without departing from the broader spirit and scope of the invention as set forth in the appended claims. The specification and drawings are, accordingly, to be regarded in an illustrative sense rather than a restrictive sense.

What is claimed is:

1. A method comprising:
    determining a first estimate of leaf positions for a plurality of leaves of a multi-leaf collimator (MLC) in a reference coordinate space based on an image generated by an image-based aperture verification system, wherein the leaf positions for the plurality of leaves define an aperture for the MLC;
    determining a second estimate of the leaf positions for the plurality of leaves in the reference coordinate space based on data from an additional source, wherein the additional source comprises an additional aperture verification system;
    generating a pictorial representation of the second estimate;
    displaying the image generated by the image-based aperture verification system; and
    displaying an overlay of the pictorial representation over the image;
    determining a first sequence of updates to the first estimate of the leaf positions based on a sequence of images generated by the image-based aperture verification system;
    determining a second sequence of updates to the second estimate of the leaf positions based on a sequence of data from the additional aperture verification system;
    synchronizing the first sequence of updates and the second sequence of updates in time;
    generating a sequence of updated pictorial representations for the second sequence of updates; and
    verifying, by a processing device, the leaf positions for the plurality of leaves based on comparing the first estimate to the second estimate, wherein the leaf positions are verified if the first estimate deviates from the second estimate by less than a threshold value.

2. The method of claim 1, further comprising:
    determining that the first estimate deviates from the second estimate by less than the threshold value for a first leaf of the plurality of leaves; and
    providing a first visual indication overlaid on the image for the first leaf.

3. The method of claim 2, further comprising:
    determining that the first estimate deviates from the second estimate by at least the threshold value for a second leaf of the plurality of leaves; and
    providing a second visual indication overlaid on the image for the second leaf.

4. The method of claim 1, wherein:
    the image-based aperture verification system comprises an image sensor offset from a beam axis of the MLC, wherein the image sensor is directed toward the plurality of leaves and generates an oblique-view image of the aperture, wherein determining the first estimate comprises transforming the oblique-view image into a top-view image having the reference coordinate space; and
    the additional aperture verification system comprises a distinct displacement gauge for each leaf of the plurality of leaves, wherein the data from the additional aperture verification comprises a plurality of leaf displacement measurements, and wherein determining the second estimate comprises transforming the plurality of leaf displacement measurements into the reference coordinate space.

5. The method of claim 1, wherein the second estimate comprises planned leaf positions of a treatment plan, the method further comprising:
displaying the image generated by the image-based aperture verification system;
mapping the planned leaf positions of the treatment plan to the reference coordinate space;
generating a pictorial representation of the planned leaf positions; and
displaying an overlay of the pictorial representation over the image.

6. The method of claim 1, further comprising:
displaying the image generated by the image-based aperture verification system;
generating a pictorial representation of the first estimate of the leaf positions; and
displaying an overlay of the pictorial representation over the image.

7. The method of claim 1, further comprising:
displaying the image generated by the image-based aperture verification system;
generating a digitally reconstructed radiograph (DRR) of a target, the DRR having the reference coordinate space and an orientation corresponding to the image; and
displaying an overlay of the DRR over the image.

8. The method of claim 1, wherein leading edges of the plurality of leaves are not shown in the image, the method further comprising:
computing positions of the leading edges based on visible portions of the plurality of leaves in the image and known offsets between the leading edges and the visible portions.

9. The method of claim 1, wherein the determining of the first estimate, the determining of the second estimate, and the verifying are performed before a radiation delivery apparatus delivers a radiation beam.

10. An apparatus comprising:
a memory; and
a processing device coupled to the memory, the processing device to:
determine a first estimate of leaf positions for a plurality of leaves of a multi-leaf collimator (MLC) in a reference coordinate space based on an image generated by an image-based aperture verification system, wherein the leaf positions for the plurality of leaves define an aperture for the MLC;
determine a second estimate of the leaf positions for the plurality of leaves in the reference coordinate space based on data from an additional source, wherein the additional source comprises an additional aperture verification system;
determine a first sequence of updates to the first estimate of the leaf positions based on a sequence of images generated by the image-based aperture verification system;
determine a second sequence of updates to the second estimate of the leaf positions based on a sequence of data from the additional aperture verification system;
synchronize the first sequence of updates and the second sequence of updates in time;
generate a sequence of updated pictorial representations for the second sequence of updates; and
verify the leaf positions for the plurality of leaves based on comparing the first estimate to the second estimate, wherein the leaf positions are verified if the first estimate deviates from the second estimate by less than a threshold value;
a display operatively coupled with the processing device, wherein the processing device is further to:
generate a pictorial representation of the second estimate;
output the image generated by the image-based aperture verification system on the display; and
output an overlay of the pictorial representation over the image on the display.

11. The apparatus of claim 10, wherein the processing device is further to:
determine that the first estimate deviates from the second estimate by less than the threshold value for a first leaf of the plurality of leaves; and
provide a first visual indication overlaid on the image for the first leaf.

12. The apparatus of claim 10, further comprising:
the image-based aperture verification system, comprising an image sensor offset from a beam axis of the MLC, wherein the image sensor is directed toward the plurality of leaves and is to generate an oblique-view image of the aperture; and
the additional aperture verification system, comprising a distinct displacement gauge for each leaf of the plurality of leaves, wherein the data from the additional aperture verification comprises a plurality of leaf displacement measurements;
wherein the processing device is further to:
map the first estimate to the reference coordinate space by transforming the oblique-view image into a top-view image having the reference coordinate space; and
map the second estimate to the reference coordinate space by transforming the plurality of leaf displacement measurements into the reference coordinate space.

13. The apparatus of claim 10, wherein the second estimate comprises planned leaf positions of a treatment plan, and wherein the processing device is further to:
output the image generated by the image-based aperture verification system on the display;
map the planned leaf positions of the treatment plan to the reference coordinate space;
generate a pictorial representation of the planned leaf positions; and
output an overlay of the pictorial representation over the image on the display.

14. The apparatus of claim 10, wherein the processing device is further to:
output the image generated by the image-based aperture verification system on the display;
generate a digitally reconstructed radiograph (DRR) of a target, the DRR having the reference coordinate space and an orientation corresponding to the image; and
output an overlay of the DRR over the image on the display.

15. The apparatus of claim 10, wherein leading edges of the plurality of leaves are not shown in the image, the processing device further to:
compute positions of the leading edges based on visible portions of the plurality of leaves in the image and known offsets between the leading edges and the visible portions.

16. The apparatus of claim 10, further comprising:
a linear accelerator; and
the MLC coupled to the linear accelerator, the MLC comprising the image-based aperture verification system and the additional aperture verification system.

* * * * *